United States Patent [19]

Friderici et al.

[11] Patent Number: 5,605,797
[45] Date of Patent: Feb. 25, 1997

[54] BOVINE β-MANNOSIDASE GENE AND METHODS OF USE

[75] Inventors: Karen Friderici, Bath; Margaret Z. Jones, East Lansing, both of Mich.; Hong Chen, Chapel Hill, N.C.; Kevin T. Cavanagh, Okemos, Mich.

[73] Assignee: Board Of Trustees Operating Michigan State University, East Lansing, Mich.

[21] Appl. No.: 306,546

[22] Filed: Sep. 15, 1994

[51] Int. Cl.$^6$ .............................. C12Q 1/68; C12P 19/34; C07H 21/02; C07H 21/04
[52] U.S. Cl. ........................... 435/6; 435/91.2; 536/23.1; 536/24.3; 536/24.31; 536/24.33
[58] Field of Search ..................... 435/6, 91.2; 536/24.3, 536/24.31, 24.33, 23.1

[56] References Cited

FOREIGN PATENT DOCUMENTS

WO93/16178  8/1993  WIPO .

OTHER PUBLICATIONS

Sommer et al, (1989), "Minimal homology requirements for PCR primers", Nucleic Acids Res. 17(16):6749.
McCabe et al, (1989), "Molecular cloning of the gene for β–mannosidase", J. Cell. Biochem. Supplement 13D:40.
Bej et al, (1991), "Amplification of nucleic acids by polymerase chain reaction (PCR) and other methods and their applications", Crit. Rev. Biochem. Mol. Biol. 26(3/4):301–344.
Stratagene catalog, (1988), p. 39.
Chen et al, (1995), "Molecular cloning and characterization of bovine β–mannosidase", J. Biol. Chem. 270(8):3841–3848.
Chen et al, (1994), "Lysosomal β–mannosidase: cDNA cloning and characterization", Am. J. Hum. Genet. 55(suppl. 3):A130.
Haithcock et al, (1995), "Molecular sequencing of caprine β–mannosidase cDNA", Am. J. Hum. Genet. 55(suppl. 3):A130.
Sopher, (1992), "Purification and characterization of caprine and bovine β–mannosidases. Characterization of a cDNa cloned with anti-β–mannosidase serum", Diss. Abstr. Int. B 1993 53(7):3460–1.
Abbitt, B. et al., J. Am. Vet. Med. Assoc. 198:109–113 (1991).
Adams, M. D. et al., Nature 355:632–634 (1992).
Ausubel, F. M. et al., Current Protocols in Molecular Biology, Greene Publishing Associates and Wiley–Interscience (John Wiley & Sons), pp. 4.2.1–4.2.5, 4.9.1–4.9.8, 6.1.1–6.1.4 and 6.4.3–6.4.4, New York (1987).
Boyer, P. J. et al., Lab. Invest. 63:100–106 (1990).
Bryan, L. et al., Biochem. Biophys. Res. Comm. 173:491–495 (1990).
Cavanagh K., Am. J. Vet. Res. 43:1058–1059 (1982).
Cheng, J. et al., Mol. Cell. Biol. 13:1892–1902 (1993).
Cooper, A. et al., N. Engl. J. Med. 315:1231 (1986).
Cooper, A. et al., J. Inherited Metab. Dis. 11:17–29 (1988).
Cooper, A. et al., J. Inherited Metab. Dis. 14:18–22 (1991).
Dorland, L. et al., J. Inherited Metab. Dis. 11:255–258 (1986).
Fisher, R. A. et al., Am. J. Hum. Genet. 41:A165 (1987).
Frei, J. I. et al., Biochem. J. 249:871–875 (1986).
Hartley, W. J. et al., Acta Neuropathol, 25:325–333 (1973).
Healy, P. J. et al., Aust. Vet. J. 57:504–507 (1981).
Iwasaki, Y. et al., J. Biochem. 106:331–335 (1989).
Jolly, R. D. et al., N. Z. Vet. J. 38:102–105 (1990).
Jones, M. Z. et al., J. Inherited Metab. Dis. 15:57–67 (1992).
Jones, M. Z. et al., J. Biol. Chem. 256:5181–5184 (1981).
Jones, M. Z. et al., J. Biol. Chem. 256:5185–5188 (1981).
Jones, M. Z., J. Neuropath. Exp. Neurol. 42:268–285 (1983).
Jones, M. Z. et al., J. Inherited Metab. Dis. 7:80–85 (1984).
Kleijer, W. J. et al., J. Inher. Metab. Dis. 13:867–872 (1990).
Kozak, M., Cell 44:283–292 (1986).
Kyosaka, S. et al., Chem. Pharm. Bull. 33:256–263 (1985).
Kyte, J. et al., J. Mol. Biol. 157:105–132 (1982).
Lathe, R., J. Mol. Biol. 183:1–12 (1985).
Levade, T. et al., Ann. Neurol. 35:116–119 (1994).
Lin, B. et al., Hum. Mol. Genet. 2:1541–1545 (1993).
Lovell, K. L. et al., J. Inherited Metab. Dis. 14:228–230 (1991).
Lovell, K. L., Acta Neuropathol. 62:121–126 (1983).
Lundin, L.–G., Biochem. Genet. 25:603–610 (1987).
Mahuran, D. J., Biochim. Biophys. Acta Mol. Basis Dis. 1096:87–94 (1991).
Mahuran, D. J. et al., J. Biol. Chem. 263:4612–4618 (1988).
Maniatis, T., et al., Molecular Cloning: A Laboratory Manual, Cold Springs Harbor Laboratory, pp. 387–389, Cold Springs, New York (1982).
O'Dowd, B. F. et al., Proc. Natl. Acad. Sci. USA 82:1184–1188 (1985).
Poenaru, L. et al., Clin. Genet. 41:331–334 (1992).
Sambrook, J. et al., Molecular Cloning: A Laboratory Manual, Cold Spring Harbor Laboratory Press, Cold Spring Harbor, pp. 5.28–5.32 and 9.52 and 9.55, New York (1989).
Sambrook, Fritsch, and Maniatis, Molecular Cloning: A Laboratory Manual, Second Edition, pp. 8.46–8.47, vol. 2, Cold Springs Harbor Laboratory, Cold Springs, New York (1989).
Sopher, B. L. et al., Biochem. J. 289:343–347 (1993).
Sopher, B. L. et al., J. Biol. Chem. 267:6178–6182 (1992).
Stein, C. et al., J. Biol. Chem. 264:1252–1259 (1989).
Stoltzfus, L. J. et al., J. Biol. Chem. 267:6570–6575 (1992).
Van Pelt, J. et al., Clin. Chim. Acta 187:55–60 (1990).
von Heijne, G. Nucleic Acids Res. 14:4683–4690 (1986).
Wenger, D. A. et al., N. Engl. J. Med. 315:1201–1205 (1986).
Wijburg, H. et al., Eur. J. Pediatr. 151:311 (1992).
Zhang, Z.–X. et al., Hum. Mol. Genet. 3:139–145 (1994).

Primary Examiner—Stephanie W. Zitomer
Assistant Examiner—Jeffrey Fredman
Attorney, Agent, or Firm—Harness, Dickey & Pierce P.L.C.

[57] ABSTRACT

The gene encoding bovine β-mannosidase has been identified, cloned, sequenced and characterized. The full-length cDNA contains 3852 nucleotides encoding 879 amino acids. The mutation involved in bovine β-mannosidosis has also been identified. Oligonucleotides and antibodies raised to the gene product are provided and are used in a variety of methods including assays to screen for an abnormal β-mannosidase gene and diagnosis of β-mannosidosis.

15 Claims, 16 Drawing Sheets

Figure 4A

```
 -74  ctcaggccgagcgtggcttccgctgccaccgcatccctcggttcttgccctgtgcggg
                                                               +1
 -14  taccgggcaacaccatgctctccgctcctgctgttgctgctggccgttgcgggct
                     M  L  L  R  L  L  L  L  L  A  P  C  G  A  G  F 47  tcgctctaccaaggtgtcagcatcagtttgcggggaaactgaagatccacagcgggaacg
  17   A  T  K  V  V  S  I  S  L  R  G  N  W  K  I  H  S  G  N  G
        ↑

107  gttcgctgcagctgccccgacggttcccggttgcgtgcacagcgcttgttcaacaaga
  37   S  L  Q  L  P  A  T  V  P  G  C  V  H  S  A  L  F  N  K  R
                                                                  *

167  ggatcatcaaggatcctctactacagattaataaccttgactatagatggatagccttgg
  57   I  I  K  D  P  Y  Y  R [F] N  N  L  D  Y  R  W  I  A  L  D
                         104r86

227  ataactggacctatatcaagaaatttaaactccactctgatatgagcacatggagtaaag
  77   N  W  T  Y  I  K  K  F  K  L  H  S  D  M  S  T  W  S  K  V
        *

287  taaatttggtttttgagggtatcgatacagttgcagtagtcctgctcaacagtgttccca
  97   N  L  V  F  E  G  I  D  T  V  A  V  V  L  L  N  S  V  P  I 347  ttggcgaaacagacaacatgttcagaagatacagctttgatattacacacgtcaaag
 117   G  K  T  D  N  M  F  R  R  Y  S  F  D  I  T  H  T  V  K  A 407  cagtgaacatcattgaggtgcgttccagtgcttccaccagtggtatatgcgaaccagagagcg
 137   V  N  I  I  E  V  R  F  Q  S  P  V  V  Y  A  N  Q  R  S  E
```

Figure 4B

```
467  aacgtcacactgcctactgggtgcccccaactgccctccacctgtcaggatggcgaat
157   R  H  T  A  Y  W  V  P  P  N  C  P  P  V  Q  D  G  E  C 527  gtcatgtcaacttattcgcaagatgcagtgttccttggatgggactgtgggacctctt
177   H  V  N  F  I  R  K  M  Q  C  S  F  G  W  D  W  G  P  S  F 587  ttcctaccagggcatctggaaagatgttagaattgaagcctataatgtttgtcatctga
197   P  T  Q  G  I  W  K  D  V  R  I  E  A  Y  N  V  C  H  L  N 647  actacttcatgttaccccatctacgataactatatgaagacatgaatcttaaaatag
217   Y  F  M  F  T  P  I  Y  D  N  Y  M  K  T  W  N  L  K  I  E
                              ─────── 142r12 ───────

707  agtcgtctttgatgtgtcagttcaaagctggtttctggtgaagcaattgtagccatcc
237   S  S  F  D  V  V  S  S  K  L  V  S  G  E  A  I  V  A  I  P 767  ctgaactaaacatacagcagactaacacattgaacttcaacatgggaaaggactgttg
257   E  L  N  I  Q  Q  T  N  N  I  E  L  Q  H  G  E  R  T  V  E 827  agctcttgtgaaaatcgacaaggctattattgtagaaacttggtggcctcatggacatg
277   S  L  F  V  K  I  D  K  A  I  I  V  E  T  W  W  P  H  G  H  G 887  gaaaccagactgggtacaacatgagcgttattttgagctggatggaggcttacgttttg
297   N  Q  T  G  Y  N  M  S  V  I  F  E  L  D  G  G  L  R  F  E
      *                                    *

947  aaaaatcagcagtaaggttatttaggacagtggaactttgtagagagccatacaaaatt
317   K  S  A  K  V  Y  F  R  T  V  E  L  V  E  E  P  I  Q  N  S
```

Figure 4C

```
1007  ctcctggtctgagtttctacttcaaaattaatggacttcccatatttctgaaaggctga
 337   P  G  L  S  F  Y  F  K  I  N  G  L  P  I  F  L  K  G  S  N 1067  attggatccctgcagattcattccaggatagagtaacctgccatgttgcgctcctct
 357   W  I  P  A  D  S  F  Q  D  R  V  T  S  A  M  L  R  L  L  L 1127  tgcagtctgtgtggatgctaacatgaatgctcttcgggtctggggaggagggagtttatg
 377   Q  S  V  V  D  A  N  M  N  A  L  R  V  W  G  G  G  V  Y  E 1187  agcaggatgaattctacgaactctgtgatgaactaggcataatgatatggcaggatttca
 397   Q  D  E  F  Y  E  L  C  D  E  L  G  I  M  I  W  Q  D  F  M 1247  tgtttgcctgtgcgctttacccaaccgataaggattcatggattctgtgagagaagaag
 417   F  A  C  A  L  Y  P  T  D  K  D  F  M  D  S  V  R  E  E  V
                    169r65/169r61

1307  tcactcaccaggtccggagagactgaaatctcatccctccatcatcacatggagtgggaata
 437   T  H  Q  V  R  R  L  K  S  H  P  S  I  I  T  W  S  G  N  N 1367  atgaaaatgaagcagcactaatgatggttggtatgatacaaagcctggctacttgcaaa
 457   E  N  E  A  A  L  M  M  G  W  Y  D  T  K  P  G  Y  L  Q  T 1427  cctacatcaaagactatgtgacactgtatgtgaaaaacatccgaacgatcgtcttagaag
 477   Y  I  K  D  Y  V  T  L  Y  V  K  N  I  R  T  I  V  L  E  G 1487  gagaccagactcgtccttttatcacatccagtcctacaaatgggccaaaaccattgcag
 497   D  Q  T  R  P  F  I  T  S  S  P  T  N  G  A  K  T  I  A  E 1547  aaggttggctctctccaaaccctatgacctgaattatggggacgtacatttttatgatt
 517   G  W  L  S  P  N  P  Y  D  L  N  Y  G  D  V  H  F  Y  D  Y
```

Figure 4D

```
1607  atgtgagtgactgctggaattggagaactttcccaaagctcgatttgtatctgatgtatg
 537   M  V  S  D  C  W  N  W  R  T  F  P  K  A  R  F  V  S  E  Y  G 1667  gatatcagtcctggccttcctcagtacattagaaaaagtttcctctgaagaggactggt
 557   Y  Q  S  W  P  S  F  S  T  L  E  K  V  S  S  E  E  D  W  S 1727  cttacagaagcagctttgcacttcatcggcaacatttgattaacggtaacaatgaaatgc
 577   Y  R  S  S  F  A  L  H  R  Q  H  L  I  N  G  N  N  E  M  L 1787  ttcaccagattgaacttcacttcaagtcccaaacagtacagatcaactacgcaggttca
 597   H  Q  I  E  L  H  F  K  L  P  N  S  T  D  Q  L  R  R  F  K
                                      *

1847  aagacactctttatctttactcaggtgatgcaggcccagtgtgtcaaaacagaaactgaat
 617   D  T  L  Y  L  T  Q  V  M  Q  A  Q  C  V  K  T  E  T  E  F
                  169r64

1907  tctaccgtcgcagtcgcagcgagatagtgaatggaaaagggcacaccatggggcgcttt
 637   Y  R  R  S  R  S  E  I  V  N  G  K  G  H  T  M  G  A  L  Y 1967  attggcagctcaatgactctggcaagctccttggtcttcttctctagagtatggaggaa
 657   W  Q  L  N  D  I  W  Q  A  P  S  W  S  S  L  E  Y  G  G  K 2027  agtggaaaatgctgcatcattactttgctcggcattcttcttcgcccctgttaccggtgggtt
 677   W  K  M  L  H  Y  F  A  R [H] F  F  A  P  L  L  P  V  G  F
                         103                              218r24

2087  ttgaggataaagatatgctttcatctatgtgctgcacacttcactcagaccagacaga
 697   E  D  K  D  M  L  F  I  Y  G  A  S [H] L  H  S  D  Q  Q  M
                     151r72
```

Figure 4E

```
2147  tgatgctcactgtgagagtccacacttggagttccctggagctcgtatgctgtctgagtcaa
 717   M  L  T  V  R  V  H  T  W  S  S  L  E  L  V  C  S  E  S  T 2207  ctaacccttcgtgataaaagctggggagtctgttctcctctatactaagccagtgcctg
 737   N  P  F  V  I  K  A  G  E  S  V  L  L  Y  T  K  P  V  P  E 2267  agttgctaaaaggatgtcccggatgtacagacaaagctgtgtggtttccttttacctgt
 757   L  L  K  G  C  P  G  C  T  R  Q  S  C  V  V  S  F  Y  L  S 2327  caactgacggggaactcttgagcccaatcaactatcactcctgtcctcactgaagaatg
 777   T  D  G  E  L  L  S  P  I  N  Y  H  F  L  S  S  L  K  N  A 2387  ccaaggggctccacaaggcaaatatcactgccaccatctcgcagcaagggacacatttg
 797   K  G  L  H  K  A  N  I  T  A  T  I  S  Q  Q  G  D  T  F  V 2447  tttttgatctgaaaacctcagctgtcgctcccctttgttggatgtaggaagcatcc
 817   F  D  L  K  T  S  A  V  A  P  F  V  W  L  D  V  G  S  I  P 2507  cagggagattcagtgacaatggtttcctcatgactgagaagacacggactgtattctttt
 837   G  R  F  S  D  N  G  F  L  M  T  E  K  T  R  T  V  F  F  Y 2567  acccttggaaaacccaccagcaagagtgaattggagcaatctttcatgtgacttcactgg
 857   P  W  K  P  T [S] K  S  E  L  E  Q  S  F  H  V  T  S  L  A
             ──── 180 ────              ──── 171 ────

2627  ctgatacttactgagggattcaggttgtatttcgagagctgaaggcaactagaaacaag
 877   D  T  Y  *
```

Figure 4F

```
2687  ttgaagaagccaggaaatgcatctgcttgctgtctggtctgttagccacttggttct
2747  cccagggaaggctgtgtatattcaggtgatgtctcaacaaagcggtgcctgggtgctgt
2807  tccgtctgcaccagggctgtgtctcttagctctcttcctttgcacctttgcaccacgtgaa
2867  tcagttctaaccaactgtcctctctcctaccccaaggaggtcctgtccacacgcagtcct
2927  ttaagggaatcacaggaacatgaccagtagccctttaagagaattacaggcacactccc
2987  aggtagccctaagggaatcacagtgaccagttgtgtatctgtggaatcaaatgtgg
3047  aagattgtgagggcatgtaggcctcaggatagctttgagaaataccaaacgattgaaa
3107  tgaaactgctttgtcattattccagaggaaatagagattcagatgttgcaacagaaaga
3167  gatgtctgggtggtagccatatggttgttgatgctggaaagtttggtgggattgattat
3227  tgccattcgattacttttgagtaggagtctttttcattgtgatttttttttttaata
3287  aaatatttgttttaacaatcacattttatttttcaaaggcaattagtagtgattcttcttttg
3347  ggaaaaaaactcacacttgaatggacatcacctttgatcatgttgaaactttttgggt
3407  gtcctgacgtaagtggtcacctgtattaagtatggcttcagattggttaagtccagtg
3467  aactttccagttcaagactatggtttgattgcatgtgagccaaagtggt
3527  attgcctttaacttgagattgaaccatttaaaaaacactgattaattataattgctatg
3587  aaatcattttgttctcatcatcctgtttataaaaattacattgatagtgaagcaagggca
3647  aaatgttaataagtagtcaatttgagtaaaggtgtataggaatattttttgttctgcttga
3707  gcaacttctgtaagtttgaaatataaaatttaagattataaattgcattgaca
3767  aaaaaaaaaaa   3778
```

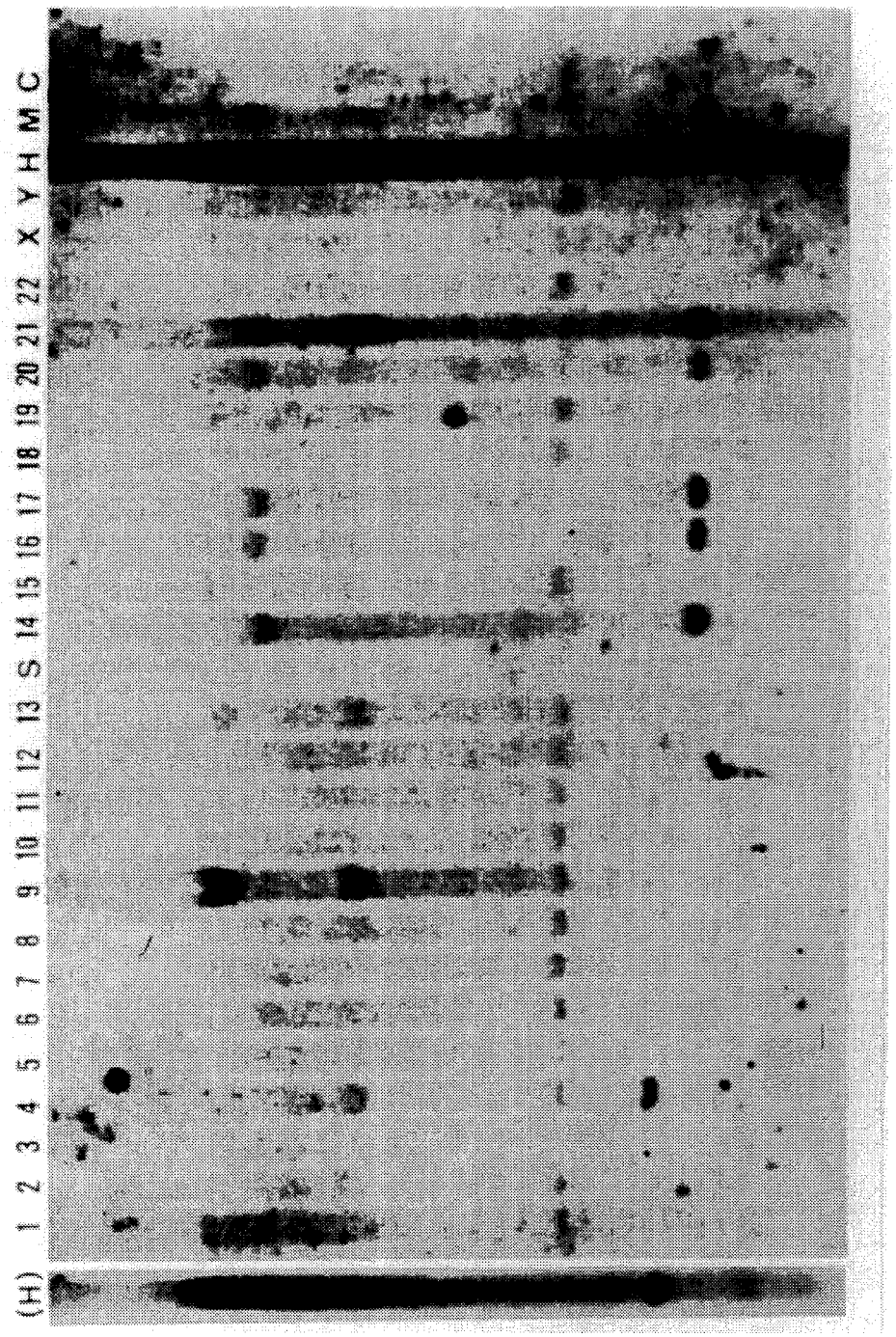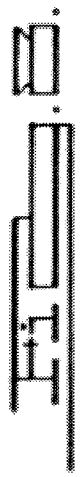

Kyte-Doolittle

Figure 10

```
         ======MJ-124======>
1 (2554) ACTGTATTCTTTTACCCCTGGAAACCCACCAGCAAGAGTGAATTGGAGCA
         TGACATAAGAAAATGGGGACCTTTGGGTGGTCGTTCTCACTTAACCTCGT
                          BstNI

ACCCCTGAAAA    Mutant Sequence
                    TGGGGACTTTT    without BstNI Site 51 (2604) ATCTTTTCATGTGACTTCACTGGCTGATACTTACTGAGGGAATCAGGTTG
          TAGAAAAGTACACTGAAGTGACCGACTATGAATGACTCCCTTAGTCCAAC 101 (2654) TATTTTCGAGAGCTGAAGGCAACTAGAAACAAGTTGAAGAAGCCAGGAAA
           ATAAAAGCTCTCGACTTCCGTTGATCTTTGTTCAACTTCTTCGGTCCTTT
                                                   BstNI 151 (2704) TGCATCTGCTTGCTGTCAGGTGTCTCGTTAGCCACTT
           ACGTAGACGAACGACAGTCCACAGAGCAATCGGTGAA
                        <======MJ-125=======
```

BOVINE β-MANNOSIDASE GENE AND METHODS OF USE

SPONSORSHIP

Work on this invention was supported in part by the National Institutes of Health Grant No. NA 16886. The government has certain rights in the invention.

FIELD OF THE INVENTION

The present invention relates generally to the gene involved in the β-mannosidosis disease process and, more particularly, to the identification, isolation, cloning and characterizing of a nucleic acid sequence corresponding to the gene encoding bovine β-mannosidase. The present invention further relates to the β-mannosidase gene product and sequence. The present invention also relates to methods of screening for carriers of the defective β-mannosidase gene and β-mannosidosis diagnosis, as well as conventional treatment and gene therapy utilizing recombinant technologies.

BACKGROUND OF THE INVENTION

Lysosomal β-mannosidase (EC 3.2.1.25) is an exoglycosidase that cleaves the single p-linked mannose residue from the non-reducing end of all N-linked glycoprotein oligosaccharides. The primary storage products associated with the enzyme deficiency are the trisaccharide Manβ1–4GlcNAcβ1–4GlcNAc and lesser amounts of the disaccharide Manβ1–4GlcNAc. Jones, M. Z. et al., *J. Biol. Chem.* 256:5181–5184 (1981) and Jones, M. Z. et al., *J. Inherited Metab. Dis.* 15:57–67 (1992). Deficiency of β-mannosidase activity results in an autosomal recessive inherited disorder, β-mannosidosis. This lysosomal storage disease was first described in Nubian goats (Hartley, W. J. et al., *Acta Neuropathol.* 25:325–333 (1973); Jones, M. Z. et al., *J. Biol. Chem.* 256:5181–5184 (1981); Healy, P. J. et al., *Aust. Vet. J.* 57:504–507 (1981) and Jones, M. Z. et al., *J. Biol. Chem.* 256:5185–5188 (1981)) and more recently has also been found in humans and cattle. Wenger, D. A. et al., *N. Engl. J. Med.* 315:1201–1205 (1986); Cooper, A. et al., *N. Engl. J. Med.* 315:1231 (1986); Dorland, L. et al., *J. Inherited Metab. Dis.* 11:255–258 (1988); Kleijer, W. J. et al., *J. Inher. Metab. Dis.* 13:867–872 (1990); Cooper, A. et al., *J. Inherited Metab. Dis.* 14:18–22 (1991); Poenaru, L. et al., *Clin Genet* 41:331–334 (1992); Wijburg, H. et al., *Eur. J. Pediatr.* 151:311 (1992) Levade, T. et al., *Ann. Neurol.* 35:116–119 (1994); Abbitt, B. et al., *J. Am. Vet. Med. Assoc.* 198:109–113 (1991); Bryan, L. et al., *Biochem. Biophys. Res. Comm.* 173:491–495 (1990) and Jolly, R. D. et al., *N. Z. Vet. J.* 38:102–105 (1990). Affected goats and cattle have very similar clinical features which include inability to stand, facial dysmorphism, intention tremors, and pastern joint hyperextension. Bryan, L. et al., *Biochem. Biophys. Res. Comm.* 173:491–495 (1990); Jolly, R. D. et al., *N. Z. Vet. J.* 38:102–105 (1990) and Jones, M. Z. et al., *J. Inherited Metab. Dis.* 7:80–85 (1984). Deafness is a consistent finding in affected goats but not in newborn calves. Widespread cytoplasmic vacuolation and dysmyelination in the central nervous system are characteristic lesions. Jones, M. Z., *J. Neuropath. Exp. Neurol.* 42:268–285 (1983) and Lovell, K. L. *Acta Neuropathol.* 62:121–126 (1983). Affected goats and calves are hypothyroid, possibly accounting for the CNS hypomyelination. Boyer, P. J. et al., *Lab. Invest.* 63:100–106 (1990) and Lovell, K. L. et al., *J. Inherited Metab. Dis.* 14:228–230 (1991). The affected ruminants display a profound deficiency of β-mannosidase activity in plasma and various tissues. Jones, M. Z. et al., *J. Biol. Chem.* 256:5185–5188 (1981); Abbitt, B. et al., *J. Am. Vet. Med. Assoc.* 198:109–113 (1991) and Cavanagh, K., *Am J. Vet. Res.* 43:1058–1059 (1982). Affected animals usually die in the neonatal period if intensive care is not provided.

In contrast with the ruminant β-mannosidosis, the human cases have a milder clinical expression and exhibit considerable heterogeneity. Wenger, D. A. et al., N. Engl. J. Med. 315:1201–1205 (1986); Cooper, A. et al., *N. Engl. J. Med.* 315:1231 (1986); Dorland, L. et al., *J. Inherited Metab. Dis.* 11:255–258 (1988); Kleijer, W. J. et al., *J. Inher. Metab. Dis.* 13:867–872 (1990); Cooper, A. et al., *J. Inherited Metab. Dis.* 14:18–22 (1991); Poenaru, L. et al., *Clin. Genet.* 41:331–334 (1992); Wijburg, H. et al., *Eur. J. Pediatr.* 151:311 (1992) and Levade, T. et al., *Ann. Neurol.* 35:116–119 (1994). Clinical expression ranges from mild peripheral neuropathy and depression (Levade, T. et al., *Ann. Neurol.* 35:116–119 (1994)) to dysmorphology, mental retardation and speech and hearing defects. Wenger, D. A. et al., *N. Engl. J. Med.* 315:1201–1205 (1986); Dorland, L. et al., *J. Inherited Metab. Dis.* 11:255–258 (1988) and Kleijer, W. J. et al., *J. Inher. Metab. Dis.* 13:867–872 (1990). In human β-mannosidosis the major accumulated product is the disaccharide Man,81–4GlcNAc. Van Pelt, J. et al., *Clin. Chim. Acta* 187:55–60 (1990) and Cooper, A. et al., *J. Inherited-Metab. Dis.* 11:17–29 (1988). Presumably the variability and severity of the mutations responsible for inactivation of β-mannosidase account for some of the phenotypic variation in the human cases. The differences in disease expression between ruminants and humans may be related to the types of mutations, species differences in development, the nature of the storage products and/or the effects on thyroid function.

Bovine β-mannosidosis has recently become a significant problem in the bovine Saler breed and in cattle cross-bred with the Saler breed. It is estimated that the number of animals at risk in North Amedca is approximately 70,000 pure-bred and 350,000–750,000 mixed-breed cattle and the carrier rate is predicted to be 20%–40%. Because β-mannosidosis is an autosomal recessive disease, carriers have one normal copy and one mutant copy of the β-mannosidase gene and although they may produce diseased offspring when bred with other carriers, they do not show any symptoms of the disease.

Presently, in order to determine whether a carrier has β-mannosidosis, the β-mannosidase enzyme activity in blood plasma or leucocytes is measured. Unfortunately this method is not very accurate because the range for the level of the enzyme in carriers overlaps with the normal range. In addition, in animals, the method is further complicated by seasonal variation of β-mannosidase levels. Moreover, the enzyme assay test cannot be used to determine carrier status in mixed-breed cattle due to species variation in enzymatic activity.

It would thus be desirable to provide the nucleotide sequence of the gene coding for β-mannosidase. It would also be desirable to provide the mutation in the nucleotide sequence of the gene coding for β-mannosidase that causes β-mannosidosis. It would further be desirable to provide the amino acid sequence of β-mannosidase. It would also be desirable to provide oligonucleotide probes for detecting the β-mannosidase nucleotide sequence and mutations therein. It would further be desirable to provide a method for detecting β-mannosidosis in a ruminant and more specifically, in a bovine. It would also be desirable to provide a method for screening for a carrier of an abnormal β-mannosidase gene. It would further be desirable to provide a diagnostic assay kit for detecting β-mannosidosis.

SUMMARY OF THE INVENTION

The bovine β-mannosidase gene has been cloned, characterized and sequenced. The cDNA contains 3852 base pairs containing a 2637-base pair coding region encoding 879 amino acids. The nucleic acid and deduced amino acid sequences of the gene are set forth in Sequence Listing ID Nos. 1 and 2, respectively, and in FIGS. 4A–4F. A mutation associated with bovine β-mannosidosis has also been discovered within the cDNA sequence of the present invention. The mutation is a single nucleotide change, an adenine (A) for a guanine (G), at position 2,648 (position 2,574 in FIGS. 4A–4F), which creates a premature stop codon in the translation of the complementary RNA sequence to protein.

With the identification and sequencing of the β-mannosidase gene and the identification of the mutation associated with bovine β-mannosidosis therein, methods for detecting an abnormal β-mannosidase gene and diagnosing β-mannosidosis are also provided. For example, oligonucleotide probes can be used within the scope of the invention in a variety of assays to screen for the presence of a normal or abnormal β-mannosidase gene or transcript. Functional assays to measure levels of gene function can also be employed for diagnosis and/or to monitor treatment. Assay kits for screening and/or diagnosis are also provided.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

FIGS. 4A–4F show the cDNA nucleotide and deduced amino acid sequences of β-mannosidase.

FIGS. 5A and 5B show an analysis of the 5' RACE products.

FIG. 8 shows a chromosome localization analysis of β-mannosidase cDNA.

FIG. 10 shows the bovine β-mannosidosis carrier test ampiicon.

DETAILED DESCRIPTION OF THE PREFERRED EMBODIMENTS

Figure 1:
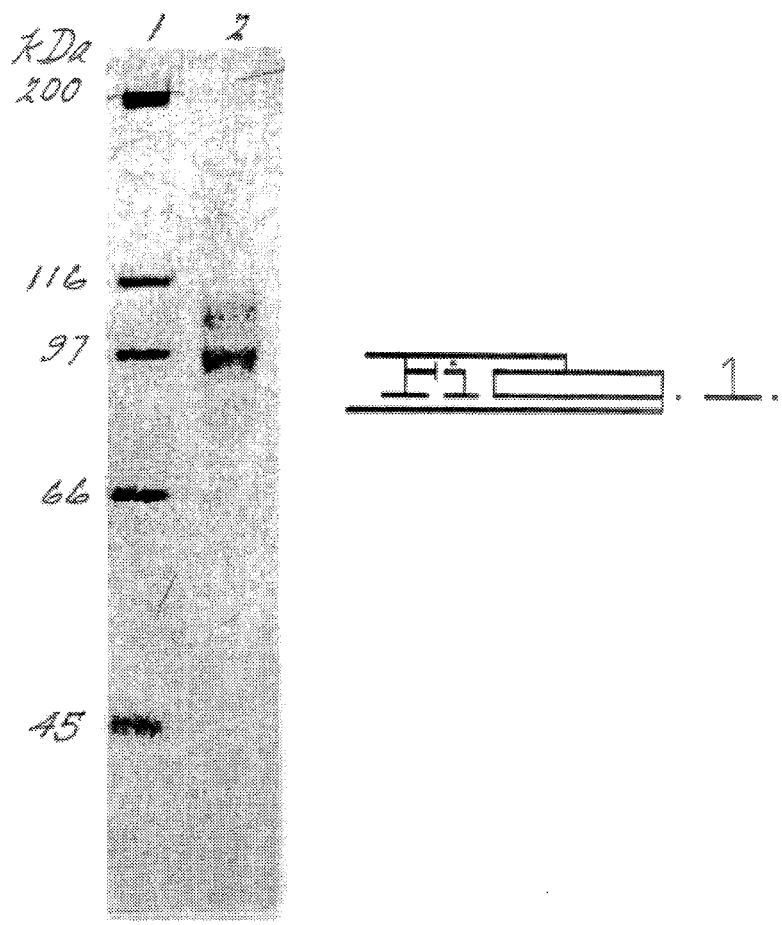
FIG. 1 is an SDS/PAGE analysis of purified β-mannosidase protein.

The full-length cDNA nucleic acid sequence for bovine β-mannosidase has been identified and is set forth in FIGS. 4A–4F and in Sequence Listing ID No. 1. The deduced amino acid sequence of the β-mannosidase cDNA is also set forth in FIGS. 4A–4F and in Sequence Listing ID No. 2. A mutation associated with bovine β-mannosidosis has also been discovered within the β-mannosidase cDNA sequence. The mutation is a single nucleotide change, an adenine (A) for a guanine (G), at position 2,648 (position 2,574 in FIGS. 4A–4F), which creates a premature stop codon in the translation of the complementary RNA sequence to protein. Oligonucleotide probes are also provided which can be used in a variety of assays to screen for the presence of a normal or abnormal β-mannosidase gene or transcript. In addition, the human chromosomal location of the β-mannosidase gene has been determined. It will thus be appreciated that the present invention provides methods for detecting an abnormal β-mannosidase gene and diagnosing β-mannosidosis. Assay kits for screening, diagnosis and/or to monitor treatment, are likewise provided.

Those skilled in the art will appreciate that with the nucleic acid and amino acid sequences of the present invention, standard mutation analysis techniques may be employed in accordance with the principles of the present invention. For example, with the knowledge of the bovine mutated nucleic acid sequence, allele specific oligonucleotides may be designed to detect the mutation in polymerase chain reaction (PCR) products that are bound to a membrane (i.e., Dot Blot Analysis). Allele specific oligonucleotides could also be bound to membranes to detect labelled PCR products from mutant or normal alleles (i.e., Reverse Dot Blot Analysis). In addition, techniques requiring the location of the mutation such as single-stranded conformational polymorphism analysis, heteroduplex analysis, and denaturing gradient gel analysis of PCR products, are also within the scope of the present invention. Moreover, other known mutation analysis methods such as Allele Refractory Mutation System and Oligonucleotide Ligation Amplification may also be employed in accordance with the principles of the present invention.

The cDNA of the present invention has been used to generate primers available for a carrier test utilizing AIRS (artificial introduction of restriction sites) and PCR technology. A detailed discussion of the assay is set forth in Specific Example 2. Generally, PCR primers are prepared wherein one primer introduces a restriction site into the normal β-mannosidase sequence and one primer will amplify genomic DNA when paired with the restriction site primer. A sample of DNA (e.g., DNA from blood cells) is amplified by PCR. The PCR products are then digested with the restriction enzyme corresponding to the introduced restriction site to provide DNA fragments. The DNA fragments are then analysed (e.g., agarose gel).

With the identification and sequencing of the β-mannosidase gene, therapy through supplementation with the normal β-mannosidase protein, whose production can be amplified using genetic and recombinant techniques, or with its functional equivalent, is also now possible. In addition, β-mannosidase may be cured or controlled through gene therapy by correcting the gene defect in situ or using recombinant or other vehicles to deliver a DNA sequence capable of expression of the normal gene product.

It will also be appreciated that the availability of the β-mannosidase cDNA allows further characterization of the structure, regulation, and expression of the gene. Further isolation of β-mannosidase cDNA from other species including human and goat and identification of molecular lesions underlying β-mannosidosis in humans, goats, and cattle is also now possible.

It will be appreciated that the term "isolated" as used herein, is meant substantially purified from the natural state through chemical, biochemical, immunological or other means, or obtained in substantially pure form by other methods known to those skilled in the art. By "substantially pure" is meant substantially free from undesirable contaminants such as other proteins. Thus, these terms are not meant to exclude synthetic and recombinant nucleic and amino acids which are contemplated within the scope of the present invention. These terms are also not meant to exclude nucleic and amino acids of the present invention which are linked, bound or intentionally combined with other moieties such as transgenes, labels, flanking amino acid sequences and the like. Furthermore, it will also be appreciated that the nucleotide and amino acid sequences of the present invention can also include some variation from the sequences represented by and complementary to the sequences set forth in the Sequence Listing but must be substantially represented by or complementary to those set forth therein. By "substantially represented by" or "substantially complementary to" is meant that any variation therein does not impair the functionality of the sequence to any significant degree. By "substantially as shown" or "substantially similar" with respect to a nucleic acid is meant sufficiently similar in structure or sequence to encode the desired polypeptide or gene product, or with respect to a polypeptide, sufficiently similar in structure or sequence to serve its principal function. Moreover, although the nucleotide sequence of the present invention is a DNA molecule, it will be appreciated that the present invention further includes nucleic acid sequences corresponding and complementary thereto.

As referred to herein, the term "nucleic acid" is intended to mean natural and synthetic linear and sequential arrays of nucleotides and nucleosides, e.g., in cDNA, genomic DNA (gDNA), mRNA, RNA, oligonucleotides, and derivatives thereof. As used herein, "A" represents adenine; "T" represents thymine; "G" represents guanine; and "C" represents cytosine; except where otherwise indicated. The term "gene" is meant any nucleic acid or reverse transcript thereof having a sequence which codes for the polypeptide or protein of interest. This term includes nucleic acids having naturally-occurring sequences as well as synthetic or any coding sequences which are capable of expression. The term "encoding" is intended to mean that the subject nucleic acid may be transcribed and translated into either the desired polypeptide or the subject protein in an appropriate expression system, e.g., when the subject nucleic acid is linked to appropriate control sequences such as promoter and enhancer elements in a suitable vector (e.g., an expression vector) and when the vector is introduced into an appropriate system or cell. The term "fragment" when used herein with reference to a nucleic acid (e.g., cDNA or gDNA) is used to mean a portion of the subject nucleic acid such as constructed artificially (e.g., through chemical synthesis) or by cleaving a natural product into a multiplicity of pieces (e.g., with a nuclease or endonuclease to obtain restriction fragments). The term "oligonucleotide" refers to a nucleic acid having a sufficient number of nucleotides which will specifically hybridize to complementary sequences under stringent conditions; that is from at least 10 nucleotides, but generally more. The term "oligonucleotide" refers to both a naturally occurring and artificial nucleic acid (e.g., a chemically synthesized nucleic acid). As one of skill in the art will recognize, "mutation" refers to any alteration of the DNA including, but not limited to, deletions, insertions and missense and nonsense mutations. One skilled in the art will also appreciate which type of mutation is being referred to from the context in which it is used.

The term "capable of hybridizing under stringent conditions" is used to mean annealing a first nucleic acid to a second nucleic acid under stringent conditions (defined below). For example, the first nucleic acid may be a test sample, and the second nucleic acid may be a portion of the nucleic acid sequence set forth in Sequence Listing ID No. 1. Hybridization of the first and second nucleic acids is conducted under stringent conditions, e.g., high temperature and/or low salt content, which tend to disfavor hybridization of dissimilar nucleotide sequences. A suitable protocol involves hybridization in 6×SSC, at 65° C. in aqueous solution or 42° C. in formamide, followed by washing with 0.1×SSC, at 65° C. in aqueous solution. (Other experimental conditions for controlling stringency are described in Maniatis, T., et al., *Molecular Cloning; A Laboratory Manual*, Cold Springs Harbor Laboratory, Cold Springs, N.Y., 1982, at pages 387–389; and also in Sambrook, Fritsch, and Maniatis, *Molecular Cloning; A Laboratory Manual, Second Edition*, Volume 2, Cold Springs Harbor Laboratory, Cold Springs, N.Y., 1989, pages 8.46–8.47). It will be appreciated, however, that although reference herein is made to nucleic acids capable of hybridizing under stringent conditions, hybridization in the practice of the present invention need not actually be conducted under such conditions.

The following Specific Examples further describe the present invention. In particular, Specific Example 1 describes the cloning and characterization of the gene encoding β-mannosidase and Specific Example 2 describes a bovine β-mannosidase carrier test. It will be appreciated that the numbering used in the Specific Examples for the nucleic acid sequence of the present invention refers to the numbering as shown in FIGS. 4A–4F (i.e., the numbering does not refer to the numbering of Sequence Listing ID No. 1, wherein the first nucleotide of the coding region of the sequence is numbered 75 instead of 1 as shown in FIG. 4A).

SPECIFIC EXAMPLE 1

Cloning and characterization of normal β-mannosidase was performed. Lysosomal β-mannosidase is expressed at very low levels in most tissues and purification of this enzyme proved difficult. Kyosaka, S. et al., *Chem. Pharm. Bull.* 33:256–263 (1985); Frei, J. I. et al., *Biochem. J.* 249:871–875 (1988); Iwasaki, Y. et al., *J. Biochem.* 106:331–335 (1989); Sopher, B. L. et al., *J. Biol Chem.* 267:6178–6182 (1992) and Sopher, B. L. et al., *Biochem. J.* 289:343–347 (1993). The production of anti-β-mannosidase monoclonal antibody permitted the establishment of a four-step chromatography procedure resulting in high purification levels of bovine β-mannosidase. Sopher, B. L. et al., *J. Biol. Chem.* 267:6178–6182 (1992) and Sopher, B. L. et al., *Biochem. J.* 289:343–347 (1993). Peptide sequence analysis of the purified protein yielded fourteen peptide sequences. Using this peptide sequence information, bovine β-mannosidase cDNA clones were sucessfully isolated, wherein the clones covered the entire coding region, the 3' non-coding region, and some of the 5' non-coding region. The following Materials and Methods, Results and Discussion further describe the present invention.

Material and Methods

Partial amino acid sequencing: β-Mannosidase protein was purified from 2.4 kg bovine kidney (Ada Beef Co., Ada, MI) using anti-β-mannosidase monoclonal antibody as described. Sopher, B. L. et al., *J. Biol. Chem.* 267:6178–6182 (1992) and Sopher, B. L. et al., *Biochem. J.* 289:343–347 (1993). The purity of the protein preparation after the Mono S step was verified by Coomassie blue staining and Western analysis. The purified protein was dialyzed against 5 mM ammonium bicarbonate solution, lyophilized, and submitted to Keck Foundation Biotechnology Resource Laboratory in Yale University for amino acid sequencing. Approximately 740 pmol of purified protein (from a total of 1240 pmol) was subjected to CNBr/trypsin digestion. Peptides were separated by C18 reverse phase HPLC. Fourteen peptides were sequenced.

Construction of synthetic oligonucleotide probes: Mixed and unique oligonucleotides were synthesized on Applied Biosystems model 394 and 380 B DNA synthesizers in the Macromolecular Structural Facility at Michigan State University. Regions with minimal codon redundancy were chosen to construct mixed oligonucleotide probes. Guessmers were constructed according to the typical codon usage frequency of human protein. Lathe, R. *J. Mol. Biol.* 183:1–12 (1985). Gene specific oligonucleotides for polymerase chain reaction (PCR) analysis were designed based on the Primer Program (Scientific & Educational Software). Synthesized oligonucleotides were reprecipitated from 2M ammonium acetate by addition of two volumes of ethanol before being used in PCR. When 5'-end labeling of the oligonucleotide was planned, the 2M ammonium acetate solution was substituted by 0.3M sodium acetate (pH 5.6). Oligonucleotides used in the screening and PCR analysis are listed in Table 1 below. In Table 1, R is G/A, Y is C/T, S is G/C, H is NC/T, D is G/A/T and N is G/A/T/C. In Table 1 oligonucleotide probes designed from sense strands are marked with underlines and guessmers are marked with double underlines. Lowercase nt represents restriction sites added to primer sequences.

cDNA library screening: Normal bovine thyroid tissue was provided to Clontech (Palo Alto, Calif.) for construction of a λJZAPII cDNA library. The bovine thyroid cDNA library, primed by both oligo-dT and random primers and consisting of $1.2 \times 10^6$ independent clones with an average insert size of 2.0 kb, was plated at a density of $1 \times 10^4$ plaque forming-units per 150 mm petri dish. In situ amplification of plaques was performed as described. Ausubel, F. M. et al., *Current protocols in molecular biology*, Greene Publishing Associates and Wiley-Interscience (John Wiley & Sons), New York (1987). The filters were prehybridized for 2 hours and hybridized for 2–3 days at 46° C.–48° C. in a solution containing 3M TMAC (Aldrich Chemical Co. Inc or Sigma) /0.1M sodium phosphate buffer, pH 6.8/1 mM EDTA, pH 8.0/5×Denhardt's solution (1% Ficoll/1% polyvinylpyrrolidone/1% bovine serum albumin)/0.6% SDS/100 µg/ml denatured herring sperm DNA (Boehringer Mannheim). Approximately $1-2 \times 10^6$ cpm/ml of 5' end-labeled mixed oligonucleotide probes with specific activity of $2-10 \times 10^6$ cpm/pmol were used during the hybridization. Filters were washed by standard procedures (Ausubel, F. M. et al., *Current protocols in molecular biology*, Greene Publishing Associates and Wiley-Interscience (John Wiley & Sons), New York (1987)) and exposed to Kodak XOMAT-AR film (Eastman KODAK Co.) at –80° C. for 1–3 days. To maximize the screening, four 17-mer mixed oligonucleotides were used sequentially for probing the filters. Previous probes were removed by incubating hybridized filters in 0.4M NaOH for 30 min at 45° C. and then 0.1×SSC solution containing 0.1% SDS and 0.2 M Tris. Cl (pH 7.5) for 30 min at 45° C. Putative positive plaques were purified through several rounds of rescreening at lower densities and then excised as pBluescript plasmids according to the manufacturer's instructions. To isolate a full-length cDNA, the 1.6 kb insert of clone 47MJ4 was isolated and labeled to a specific activity of $1.4 \times 10^9$ cpm·µg. Up to $1 \times 10^6$ cpm/ml of the denatured probe was added in a 5×SSPE hybridization solution containing 50% formamide (Boehringer Man-

TABLE 1

| Probe or PCR primer | Peptide # or bp pos. | Oligonucleotide Sequence (5"→3") |
|---|---|---|
| MJ4 | 218r24 | GGNTTYGARGAYAARGA SEQ ID NO. 5 |
| MJ48 | 142r12 | TARTTRTCRTADATNGG SEQ ID NO. 6 |
| MJ63 | 169r61 | CCRAARTCYTTRTCNGT SEQ ID NO. 7 |
| MJ64 | 104r86 | ATHAARGAYCCNTAYTA SEQ ID NO. 8 |
| MJ7 | 218r24 | TCCTTCTTTGCCCCCCTGCTGCCTGTGGGCTTTGAGGACAAGGA SEQ. ID NO. 9 |
| MJ23 | 151r72 | CTGTTCATCTATGGCGCCTCTGACCTGCACTCTGAC SEQ ID NO. 10 |
| MJ65 | 171 | GACTGGAGCAGTCCTTCCATGTGACCTCCCTGGCTGACACCTAC SEQ ID NO. 11 |
| MJ100 | 814 bp | CACAAAGAGCTCAACAGTCCTTTC SEQ ID NO: 12 |
| MJ101 | 780 bp | AGGTCAATGTTGTTTGTCTGCTGT SEQ ID NO: 13 |
| MJ110 | 636 bp | GCtctagaAACATGAAGTAGTTCAGATGACAA SEQ ID NO: 14 |
| MJ66 | 103 | CTggatccATGCTNCATYATYTTSC SEQ ID NO: 15 |
| MJ5 | 180 | ACgtcgscggYTTCCANGGRTARAARAA SEQ ID NO: 16 |

Labeling probes: Oligonucleotide probes were prepared by 5' end labeling. Each 20 ul reaction contained 10 pmol of oligonucleotide, 15 pmol of $^{32}$P[γ-ATP] (6000 Ci/mmole, 10 mCi/ml, NEN/Du Pont), 1 ul of 20×buffer (Boehringer Mannheim), and 10 units of T4 polynucleotide kinase (Boehringer Mannheim) and was incubated at 37° C. for one hour. Unincorporated nucleotides were removed using an Nuctrap push column (Stratagene) following the manufacturer's instructions. cDNA fragments were labeled by the random primed method (Boehringer Mannheim) using $^{32}$P [a-dCTP](3000 Ci/mmole, Amersham).

nheim)/0.5% SDS/5×Denhardtx s solution/10/Tg/ml denatured herring sperm DNA to reprobe original filters at 42° C. After approximately 20 hours incubation, the filters were washed in 2×SSC/0.1% SDS, 2×10min at room temperature, then washed until a low background signal was achieved. The final wash was 0.1×SSC/0.1% SDS solution at 65° C. for 30 min.

cDNA synthesis and Polymerase chain reaction: Total RNA (10 µg) or poly $A^{+\ mRNA}$ (1 µg) was heated at 65° C. for 5 min, then incubated with 10 µl of 5 ×reverse transcription buffer (Gibco BRL), 5 μl of 0.1M dithiothreitol (DTT), 5 μl of 10 mM dNTP mixture, 1.5 μl of 40 unit/μl RNasin (Promega), 5 to 75 pmol of antisense oligonucleotides and 200–400 units of M-MLV reverse transcriptase (Gibco BRL) in 50 μl of reaction mixture at 37° C. for one hour. Synthesized first strand cDNAs were precipitated by adding an equal volume of 4M ammonium acetate acid and two volumes of ethanol and resuspended in 50 μl of distilled water. An aliquot (1–2 μl) of the cDNAs was amplified in a 50 μl reaction volume by AmpliTaq DNA polymerase (Perkin-Elmer Cetus) in the GeneAmp PCR system 9600 (Perkin-Elmer Cetus). Generally, 30–35 PCR cycles were performed and each PCR cycle consisted of 45 seconds denaturation at 94° C., 1 min annealing at 46° C.–55° C., and 1 min extension at 72° C. A 5 min predenaturation at 95° C. and an additional 10 min extension at 72° C. were applied before and after the cycle reactions, respectively. One fourth of the amplified product was analyzed by electrophoresis on Nusieve 3:1 agarose gels (FMC BioProducts). To perform reamplification and nested PCR, agarose containing the band of interest was removed using a capillary tube. The agarose was either used directly (5 μl) in reamplification reactions or diluted in distilled water, and aliquots of agarose suspension were used in PCR reactions.

To analyze putative clones, PCR was performed using either plasmid DNA or crude phage lysates as templates. The crude phage lysates were prepared by adding an equal volume of 0.1M NaOH to an aliquot of phage stock, incubating for 10 min at 95° C., and then neutralizing by adding 1/20 volume of 2M Tris. CI (pH 7.5). To determine the orientation of an insert, PCR was accomplished by using a gene specific primer (either unique or degenerate) and a M13 primer (reverse or –21 primer). To clone the 5' region of β-mannosidase cDNA, the 5' RACE system kit (Gibco BRL) was used according to the manufacturerxs instructions. About 0.5 μg poly A+ mRNA of bovine thyroid was copied into single strand cDNAs using a gene specific primer MJ100 designed from the antisense strand of the 5' end of clone 17MJ48. The cDNA was tailed with homopoly-dC and then amplified by an anchor primer (AP) (Gibco BRL) and a nested gene specific primer, MJ101. The 950 base pair product was gel purified and reamplified by a universal amplification primer (UAP) and the primer MJ101 and by UAP and a nested degenerate primer MJ48. The specific PCR products were gel purified on 1% Nusieve GTG agarose (FMC BioProducts) and directly sequenced by a nested antisense primer MJ110 and cloned into the pCR™ II vector using a TA Cloning system (Invitrogen). Clones containing the correct insert size were subjected to sequencing.

RNA isolation and Northern blot hybridization: Total RNA was extracted from various bovine and caprine tissues and from both normal and affected animals according to standard procedures. Ausubel, F. M. et al., *Current protocols in molecular biology*, Greene Publishing Associates and Wiley-Interscience (John Wiley & Sons), New York (1987). Poly A+ RNA was isolated using a poly A+ quick mRNA kit (Stratagene). Poly A+ RNA samples were analyzed by electrophoresis on a 1% agarose gel containing 2.2M formaldehyde as described (Ausubel, F. M. et al., *Current protocols in molecular biology*, Greene Publishing Associates and Wiley-Interscience (John Wiley & Sons), New York (1987)) and blotted on the Hybond-N membrane (Amersham). Northern hybridization was performed by standard procedures (Sambrook, J. et al., *Molecular Cloning: A Laboratory Manual*, Cold Spring Harbor Laboratory Press, Cold Spring Harbor, New York (1989)) using radiolabeled 47MJ4 insert, or the EcoRI fragment of 17MJ48 and a PCR product from 46MJ4 as probe(s). Filters were washed in a step-wise fashion according to the background signal with a final wash in 0.5×SSC/0.1% SDS for 30 min at 42° C. The filters were exposed at –80° C. for 10 days. After removal of the β-mannosidase probe, the blot was rehybridized to a cDNA probe of rat glyceraldehyde-3-phosphate-dehydrogenase (GAPDH) to normalize the amounts of RNA.

DNA sequencing and computer analysis: Double strand DNA was prepared using Magic (Wizard) minipreps DNA purification system (Promega). Sequencing was carried out by the Taq cycling method using either dye terminators or dye primers (M13 –21 primer and M13 reverse primer) on a 373A DNA sequencing system (Applied Biosystems) in the DNA Sequencing Facility at Michigan State University. The entire inserts in clones 46MJ4, 47MJ4, 17MJ48, and C2U48 were sequenced from both strands using internal oligonucleotide primers. PCR products were either directly sequenced after purification on 1% Nusieve GTG low melting agarose gel (FMC BioProducts) or were cloned into pCR™II vector using the TA cloning kit. Plasmid DNAs were then prepared and sequenced as described above. DNA sequencing analysis and homology search against GenBank were performed using GCG program version 7, Apr., 1991 (Genetics Computer Group DNA Sequence Analysis Software).

Southern hybridization analysis: A DNA panel of 24 human/rodent somatic cell hybrids was obtained from Coriell Cell Repositories, Coriell Institute for Medical Research (Camden, N.J.). Approximately 15 μg of DNA of each hybrid was digested by PstI and separated on a 1% agarose gel. A PCR product of clone 46MJ4 was labeled by random priming to a specific activity of $4 \times 10^8$ cpm/μg and used as a probe in the Southern blot analysis. Hybridization was carried out in 50% formamide/6×SSC/5×Denhardtxs/0.5% SDS/100 μg/ml denatured herring sperm DNA for 20 hours at 42° C. The final wash was in 0.2×SSC/0.1% SDS for 15 min at 65° C. (high stringency wash) or 1×SSC/0.1% SDS for one hour at 65° C. (low stringency wash). The blot was exposed to Kodak XOMAT-AR film at –80° C. for 3 to 10 days. For zoo blots DNAs from human, mouse, rat, goat, cattle, and Chinese hamster were isolated and digested with different restriction enzymes by standard procedures. Sambrook, J. et al., *Molecular Cloning: A Laboratory Manual*, Cold Spring Harbor Laboratory Press, Cold Spring Harbor, New York (1989). Southern hybridization was carried out essentially the same as described above.

Results

Peptide sequencing: Bovine β-mannosidase was purified approximately 150,000 fold by a four-step chromatography procedure. An aliquot (12 pmoles) of purified β-mannosidase protein was fractionated on 7.5% SDS-PAGE and visualized by Coomassie blue staining. As shown in FIG. 1, wherein lane 2 is the β-mannosidase protein and lane 1 is the high range SDS-PAGE standard (Bio-Rad), two predominant peptides of ca. 100 and 110 kDa were revealed, with 100 kDa being the major peptide. Both peptides represent β-mannosidase as shown in previous studies (Sopher, B. L. et al., *J. Biol. Chem.* 267:6178–6182 (1992) and Sopher, B. L. et al., *Biochem. J.* 289:343–347 (1993)) and as demonstrated by reaction with anti β-mannosidase polyclonal serum (data not shown).

Figure 2A:
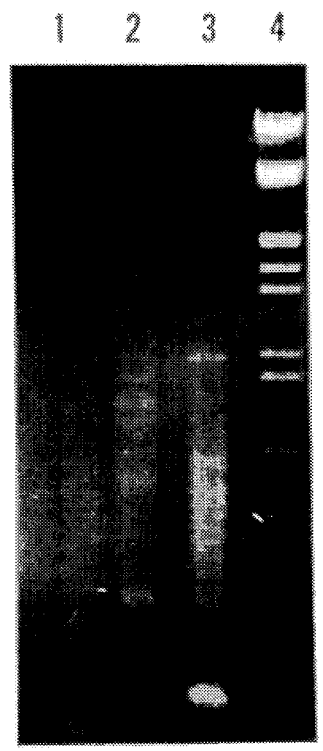
FIG. 2 is a reverse phase HPLC profile of CNBr/tryptic cleaved peptides of β-mannosidase.
Figure 2:
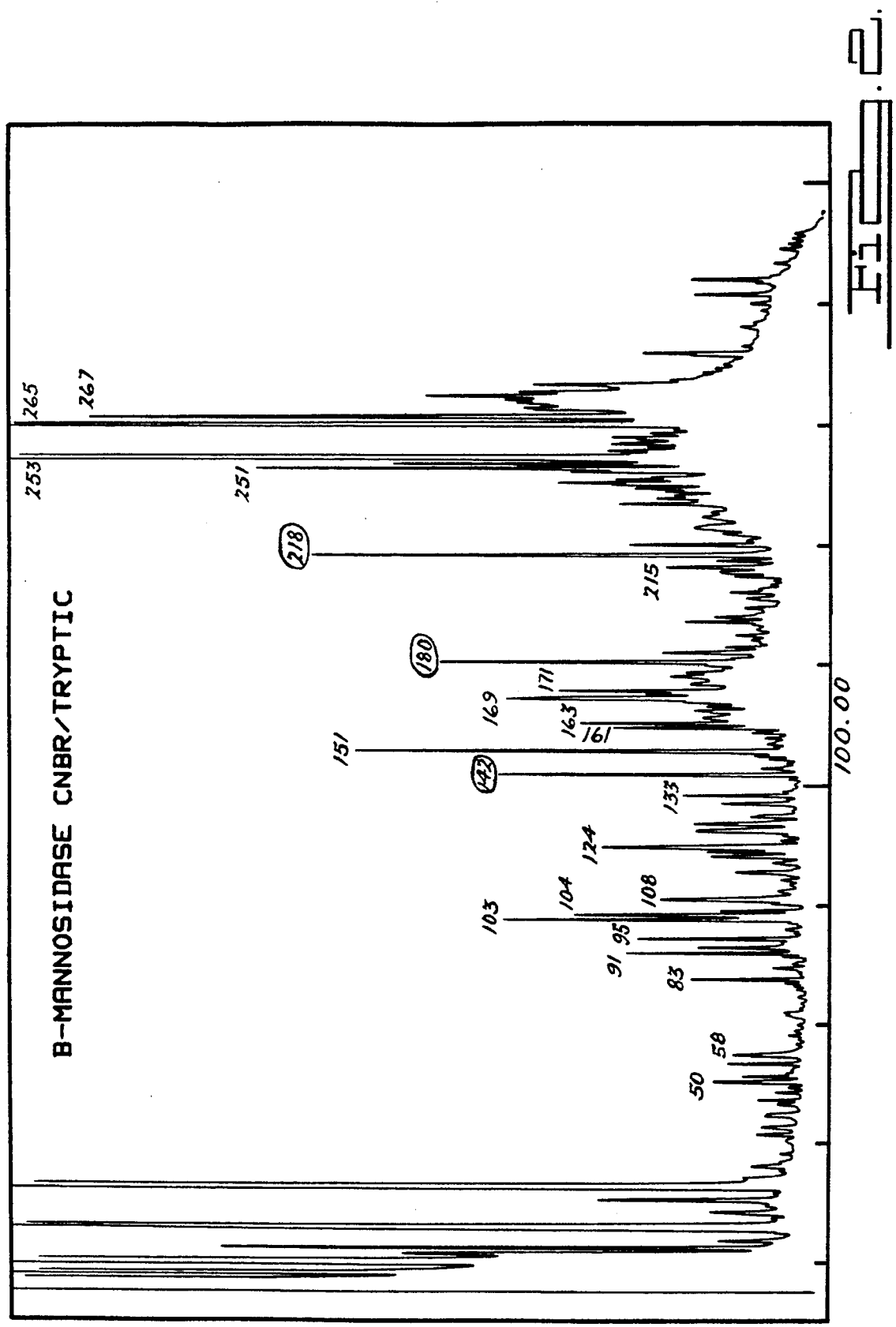

Previous studies have suggested that the N-terminus of β-mannosidase protein was blocked. In addition, trypsin cleaved peptides appeared to be relatively insoluble. Therefore, the purified protein was subjected to combined CNBr and trypsin digestions. Approximately 750 pmol β-mannosidase protein purified by the four-step column purification were subjected to CNBr and typsin digestions and separated by C18 reverse phase HPLC. As shown in FIG. 2, fractionation of the CNBr/tryptic digest yielded multiple peptides suitable for direct sequencing or sequencing after rechromatography. Peptides 103, 171, 180 and 253 were sequenced directly, mixed sequences were obtained form peptide 253, peptides 104, 142, 151,189, 218, 251,285 and 287 were subjected to repurification before sequencing, and peptides 251,265 and 267 did not yield sequence.

As shown in Table 2 below, sequencing of fourteen peptides including those repurified by reverse phase HPLC resulted in a total of ten non-overlapping peptides with complete sequences plus additional peptides with incomplete or mixed sequences. Four peptide sequences (142r12, 150r72, 218r24, and 103) were found to match previous peptide sequences (1*, 2*, and 3* in Table 2) resulting from sequencing of CNBr peptides of a deglycosylated gel purified 86 kDa protein (corresponding to the 100 kDa glycosylated β-mannosidase protein). In Table 2, the homology is shown by :, amino acids in parentheses were identified ambiguously and peptides which produced limited partial sequences or a mixture of more than two sequences are not listed. Searches with all peptide sequences obtained revealed no significant homologies with existing proteins in the GenBank, SwissProt or EMBL databases.

adopted. First, bovine thyroid gland, the tissue showing the highest expression of β-mannosidase activity, was used to construct a cDNA library to enrich for β-mannosidase transcripts. Second, oligonucleotides that gave a good signal in previous studies or that were derived from peptide sequences (e.g. 142r12) produced by two different sequencing sources were used for screening. Third, in an effort to increase detection levels, in situ amplification of plaques was performed. Ausubel, F. M. et al., *Current protocols in molecular biology,* Greene Publishing Associates and Wiley-lnterscience (John Wiley & Sons), New York (1987). Finally, multiple oligonucleotides and sequential hybridization were used.

By screening approximately $5 \times 10^5$ phage from the bovine thyroid cDNA library sequentially with four different degenerate oligonucleotides, MJ4,MJ48, MJ63, and MJ64, a total of 19 positive clones were detected. Of the 19 positive clones, three clones identified with MJ4 (43MJ4, 46MJ4, and 47MJ4) also hybridized with guessmers MJ7,MJ23, and MJ65. These oligonucleotides correspond to three different non-overlapping peptides, suggesting clones 43MJ4, 46MJ4, and 47MJ4 are likely to be genuine positive clones. These three clones were plaque purified, excised as pBluescript plasmids, and subjected to further analyses. Restriction enzyme digestion showed that clones 43MJ4 and 47MJ4 each contained a ~1.6 kb insert with identical restriction maps, indicating that they were from the same clone, while clone 48MJ4 contained an insert of ~1.8 kb with a

TABLE 2

| Peptide | Sequence |
|---|---|
| 142r12 | F T P I Y D N Y (M) SEQ ID NO: 17 |
| | . . . . . |
| | . . . . . |
| | . . . . . |
| 1* | F T P I Y D SEQ ID NO: 18 |
| 151r72 | L F I Y G A S D L H S D Q Q (M) SEQ ID NO: 19 |
| | . . . . . . . . . . |
| | . . . . . . . . . . |
| 2* | (G/L) (A/Y) (S/P) (D/T) L (H/K) (S/D) F (Q/E) SEQ ID NO: 20 |
| 218r24 | (S/P) (F/R) (F/Q/P) (A/K) P (L/G) (L/P) (P/A) (V/E) G F E D K D (T) SEQ ID NO: 21 |
| | . . . . . . . . |
| | . . . . . . . . |
| 3* | ? ? Y F A ? ? F F A ? ? L SEQ ID NO: 22 |
| | . . . . . . |
| | . . . . . . |
| 103 | (L/D) H Y F A R |
| 104r86 | (I/G) I K D P Y Y R R SEQ ID NO: 23 |
| 180 | T V F F Y P W K P (M) SEQ ID NO: 24 |
| 169r64 | F K D T L Y L T Q V (M) SEQ ID NO: 25 |
| 171 | (T/A) E L E Q S F H V T S L A D T Y SEQ ID NO: 26 |
| 169r65 | F A C A L Y P T D K D F (M) SEQ ID NO: 27 |
| 169r61 | F A C A L Y P T D K D F G SEQ ID NO: 28 |

Isolation and characterization of cDNA clones: Previous attempts at cloning β-mannosidase cDNA include immunoscreening using anti-β-mannosidase polyclonal antibodies (Sopher, B. L. et al., *J. Biol. Chem.* 287:6178–6182 (1992) and Sopher, B. L. et al., *Biochem. J.* 289:343–347 (1993)), plaque hybridization using several mixed oligonucleotides or guessmers derived from peptide sequences and PCR with various combinations of degenerate oligonucleotide primers. All these attempts were performed without success presumably because of the very low level of expression of this lysosomal enzyme. The following strategy was thus restriction map similar to the other two clones. Sequence analysis revealed that clones 43MJ4 & 47MJ4 (referred to as 47MJ4 in all later sections), and 46MJ4 all started at the same 5' nucleotide which corresponded to a cleaved internal EcoRI site and contained an open reading frame of 730 bp. There were two nucleotide differences between clones 46MJ4 and 47MJ4: C at position 2418 was replaced by G in clone 47MJ4 with no impact on the amino acid sequence, while C at position 2125 was substituted by T in clone 47MJ4, resulting in an amino acid change (H709D). The aspartic acid (D) was found in that position in the direct peptide sequence of peptide 151r72. The sequence homology between clones 46MJ4 and 47MJ4 diverged at 1182 base pair from their 5' ends. The authenticity of both clones was established by colinearity of the predicted amino acid sequence of the two clones with five microsequenced peptide sequences (103, 218r24, 151r72, 180, and 171).

Figure 3:
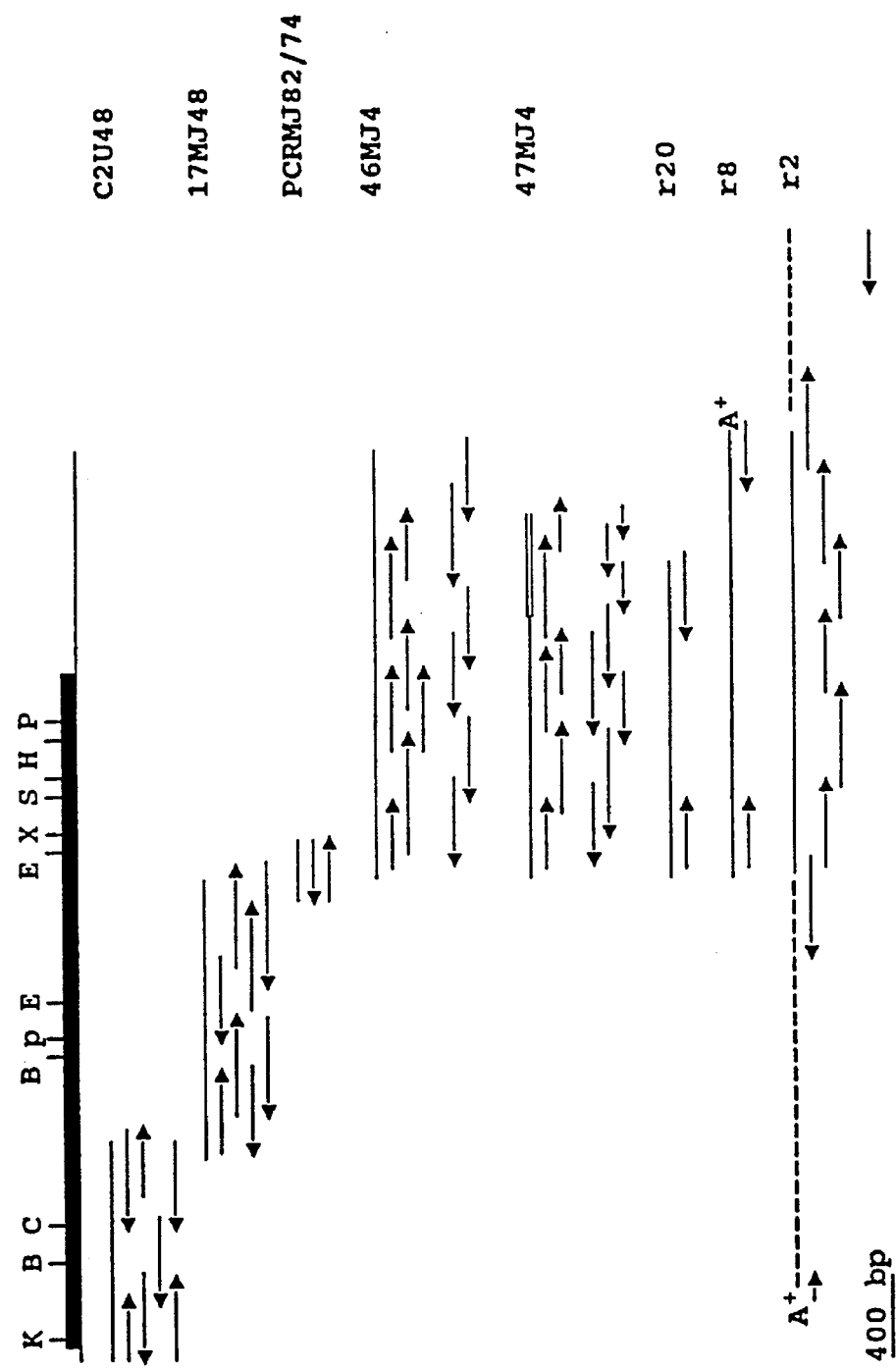
FIG. 3 is a restriction map and sequencing strategy for β-mannosidase cDNA clones.

FIG. 3 is a restriction map and sequencing strategy for β-mannosidase cDNA clones. In FIG. 3, C2U48 is a clone of the 5' RACE product; PCRMJ82/74 is a PCR product generated using primers from clones 17MJ48 and 46MJ4 sequence information; solid bar represents a coding region; double line and dash line represents no homologies with 46MJ4; K represents KpnI; B represents BamHI; C represents ClaI; E represents EcoRI; X represents XbaI; S represents SalI; H represents HincII; p represents PstI; P represents PvII and $A^+$ represents the poly (A) tail.

To isolate a full-length cDNA, the 1.6 kb insert of clone 47MJ4 was gel purified, labeled, and used to probe the original filters. Three additional clones (r2, r8, and r20) were identified. EcoRI digestion of plasmid DNAs indicated clone r20 lacked one of the EcoRI sites in the cloning site and contained an insert of approximately 1.4 kb. The insert size of clone r8 was close to 1.8 kb. Clone r2 appeared to have a large insert of approximately 4.3 kb, which was confirmed by Southern hybridization of EcoRI digested plasmid and phage DNA. Analysis of these clones by PCR indicated that clone r2 contained approximately 1.2 kb more sequence in the 5' end than the existing clones. The r8 and r20 clones appeared to also start at the same internal EcoRI site as clones 46MJ4 and 47MJ4 (see FIG. 3). Their 3' end sequences were nearly identical to that of clone 46MJ4, with clone r8 containing 20 additional base pairs including a short poly (A) tail (see FIG. 3). Clone r2 encompassed most of the sequence of clone 46MJ4. However, the sequence homology diverged at 86 base pair upstream of the 3' end of clone 46MJ4, and a long stretch of poly (A) tail was present in the 5' end. Furthermore, no open reading frame was found before the EcoRI site and the internal sequence homology with the 5' end of clones 46MJ4 and 47MJ4 ceased right at the EcoRI site of clone 46MJ4. These results clearly indicated that the EcoRI sites of these clones were not methylated by EcoRI methylase during the construction of this bovine thyroid cDNA library. Additional cloning artifacts occurred with clone r2.

FIGS. 4A–4F are the nucleotide and deduced amino acid sequences of the β-mannosidase cDNA. In FIGS. 4A–4F, nucleotides upstream of the predicted initiation codon ATG are given negative numbers. Potential N-glycosylation sites are indicated by ★. Colinear CNBr/Tryptic peptides are underlined. Residues which do not match with peptide sequences determined by microsequencing are marked with [ ]. The two possible polyadenylation sites are underlined. The signal peptide sequence is double underlined. The arrow indicates the predicted signal peptide cleavage site.

The discovery of the failure of EcoRI methylation led to the reevaluation of two clones which had been identified previously by a mixed oligonucleotide probe (MJ48) in the initial screening. The peptide sequence corresponding to probe MJ48 was not found in the initial clones obtained, thus clones identified by MJ48 might correspond to sequence upstream of the cleaved EcoRI site. If their internal EcoRI site(s) was cleaved due to inefficient EcoRI methylation, these clones would not cross-hybridize with the three guessmers MJ7, MJ23, and MJ65, which were all located downstream of the EcoRI site. To evaluate these clones, PCR was performed on crude phage lysates and plasmid DNA from clones 9MJ48 and 17MJ48 using vector primers (M13 forward or reverse primer) and oligonucleotide primers for peptides not found in the original clones. Gene specific PCR products were produced from clone 17MJ48. Sequence analysis showed that clone 17MJ48 contained an insert of 1119 base pair and encoded 373 amino acids. Four additional peptide sequences (169r64, 169r65, 169r61, and 142r12) were found to match exactly with the predicted amino acid sequence of clone 17MJ48 (see FIG. 4). This clone contained an internal EcoRI site and ended at an EcoRI site that had no linker sequences (see FIG. 3). To show that clones 46MJ4 and 17MJ48 were continuous, PCR primers designed from each clone were used to produce the predicted amplification products from cDNA initiated by a downstream primer (see FIG. 3).

Figure 5B:
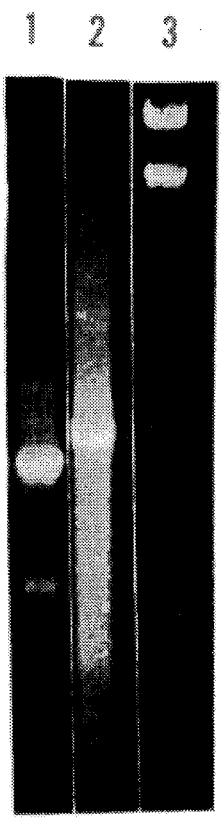

Clone 17MJ48 plus clone r8 yielded a cDNA construct of about 3 kb. However, northern hybridization indicated that the mRNA was 4.2 kb (data not shown). In order to isolate the missing 5' end of the β-mannosidase gene, 5' rapid amplification of cDNA ends (RACE) (BRL) was adopted and the results are shown in FIGS. 5A and 5B. In FIG. 5A, poly dC-tailed cDNA reverse transcribed using MJ100 from 0.5 μg bovine thyroid poly $(A)^+$RNA was amplified in a 50 μg PCR reaction by a gene specific primer MJ101 and an anchor primer. After 35 cycles (94° C. 1 min, 57° C. 30 seconds, and 72° C. 2 min for each cycle) of amplification, 20 μl were loaded into 1% agarose gel. Lane 1 shows the negative control without cDNA, lane 2 shows the PCR of non-tailed cDNA, lane 3 shows the PCR of poly dC-tailed cDNA and lane 4 shows 1 μl of marker III (lambda DNNEcoRIIHindIII). The major product of 950 bp in lane 3 from panel A was excised and suspended in 30 μl water. Aliquots of the suspension were reamplified with nest primers in a reaction of 200μl. The results are shown in FIG. 5B, wherein lane 1 shows the PCR with MJ48 and UAP, lane 2 shows the PCR with MJ101 and UAP, and lane 3 shows the marker III.

As shown in FIG. 5A, amplification of dC-tailed bovine cDNA by a gene specific oligonucleotide primer (MJ101) and adapter primer produced a smear background with a discrete band of approximately 950 base pair (see FIG. 5A, lane 3). The 950 base pair product was gel purified and reamplified by UAP and the oligonucleotide primer (MJ101) and by UAP and a nested degenerate primer (MJ48). A predominant PCR product of approximately 950 base pair was produced using the first pair of oligonucleotide primers (see FIG. 5B, lane 2). Two PCR products with a major product being ~770 bp, were observed using the second pair (see FIG. 5B, lane 1). The reamplified 950 base pair product and 770 base pair product were gel purified and cloned into pCR™II vector. Positive subclones, identified by PCR using a nested gene-specific oligonucleotide (MJ110) and M13 reverse or forward primer, were sequenced. The authenticity of the 5' RACE product was confirmed by both direct sequencing of the PCR products using primer MJ101 and sequencing of two positive subclones from 950 base pair and 770 base pair PCR product, respectively. Besides the expected peptide 142r12 also present in the 5' end of clone 17MJ48, a new peptide sequence (104r86) was identified in the deduced amino acid sequence of the 5' RACE products. In addition, the sequence of the 5' RACE products also revealed a possible translation initiation codon at nucleotide 75 of the clone followed by an open reading frame. The nucleotides flanking the ATG (ACCATGC) were in good agreement with the consensus sequence for the eukaryotic initiation codon: A/GCCATGG. Kozak, M. *Cell* 44:283–292 (1986). Furthermore, the 17 amino acid residues following the initiation codon exhibited features characteristic of a signal sequence (von Heijne, *G. Nucleic Acids Res.* 14:4683–4690 (1986)), i.e. a basic N-terminal region, a central hydrophobic region, and a more polar C-terminal region.

Figure 6:
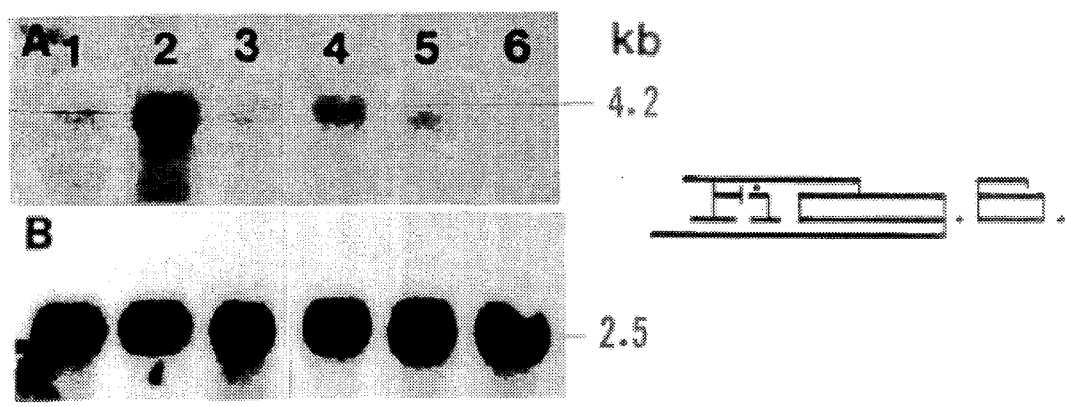
FIG. 6 shows a Northern hybridization analysis of normal tissues and affected animal tissues hybridized to β-mannosidase probes.

Northern blot analysis: A Northern blot hybridization analysis of normal tissues and affected animals was performed. Poly A⁺RNA samples isolated from various bovine and caprine tissues were hybridized to a cDNA probe generated by PCR of clone 46MJ4 using primers MJ66 and MJ5 and an EcoRI fragment of clone 17MJ48. The blot was hybridized for two days and washed finally in 0.5×SSC/ 0.1% SDS at 42° C. for 30 min. The film was exposed for 10 days at −80° C. In FIG. 6, lane 1 shows affected bovine thyroid, lane 2 shows normal bovine thyroid, lane 3 shows affected bovine kidney, lane 4 shows normal goat liver, lane 5 shows normal goat kidney and lane 6 shows affected goat kidney. FIG. 6, panel B, shows the results of rehybridization to a rat GAPDH cDNA probe after removal of the β-mannosidase probe. As shown in FIG. 6, a single transcript of approximately 4.2 kb was observed in both normal and affected tissues as well as in both caprine and bovine tissues by using the cloned cDNA as probes. The amount of transcript in affected tissues was significantly decreased compared to their normal counterparts. Thyroid tissue showed the highest mRNA level.

Figure 7A:
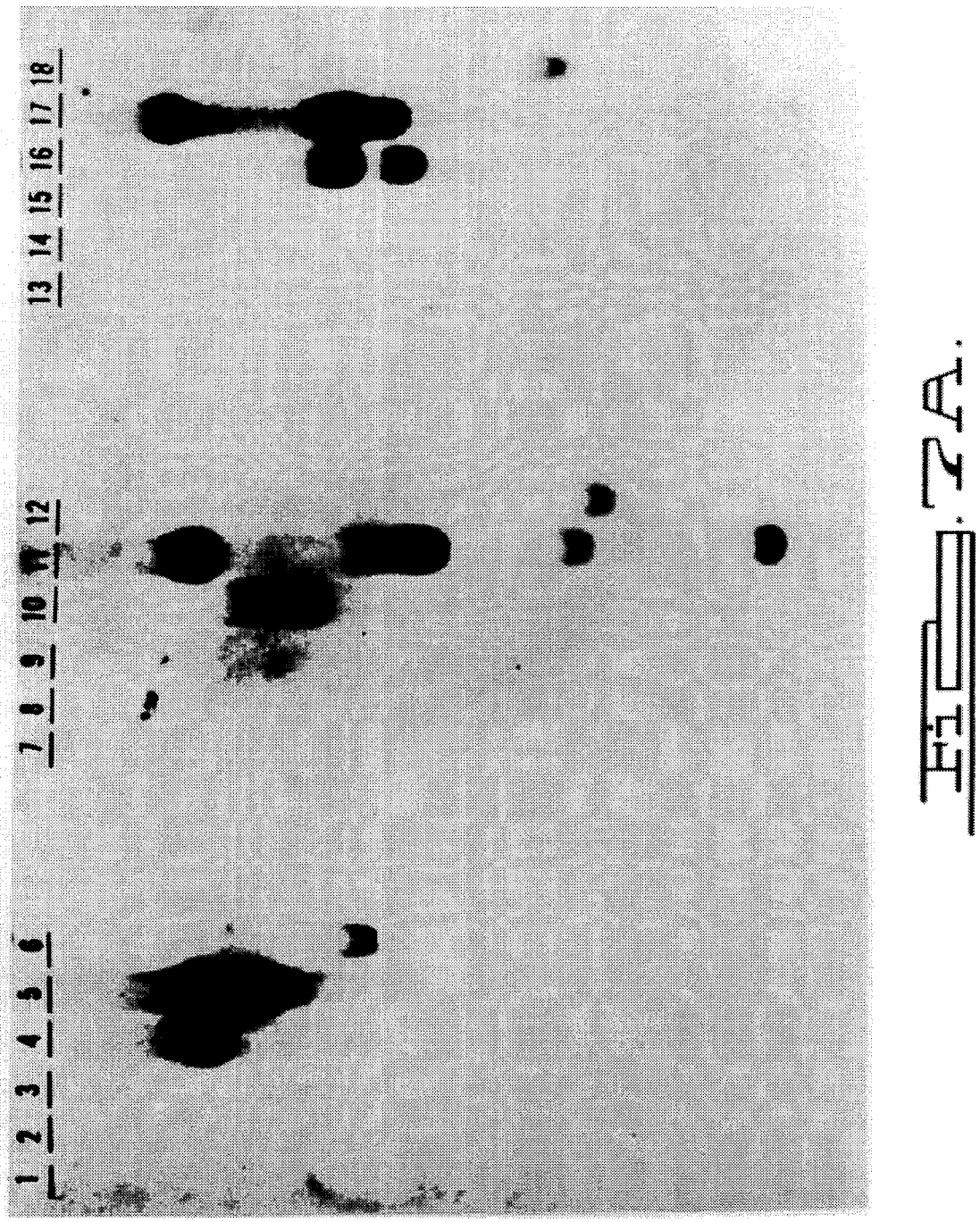
FIGS. 7A and 7B show a Southern hybridization analysis of genomic DNA from various species hybridized to a β-mannosidase probe.
Figure 7B:
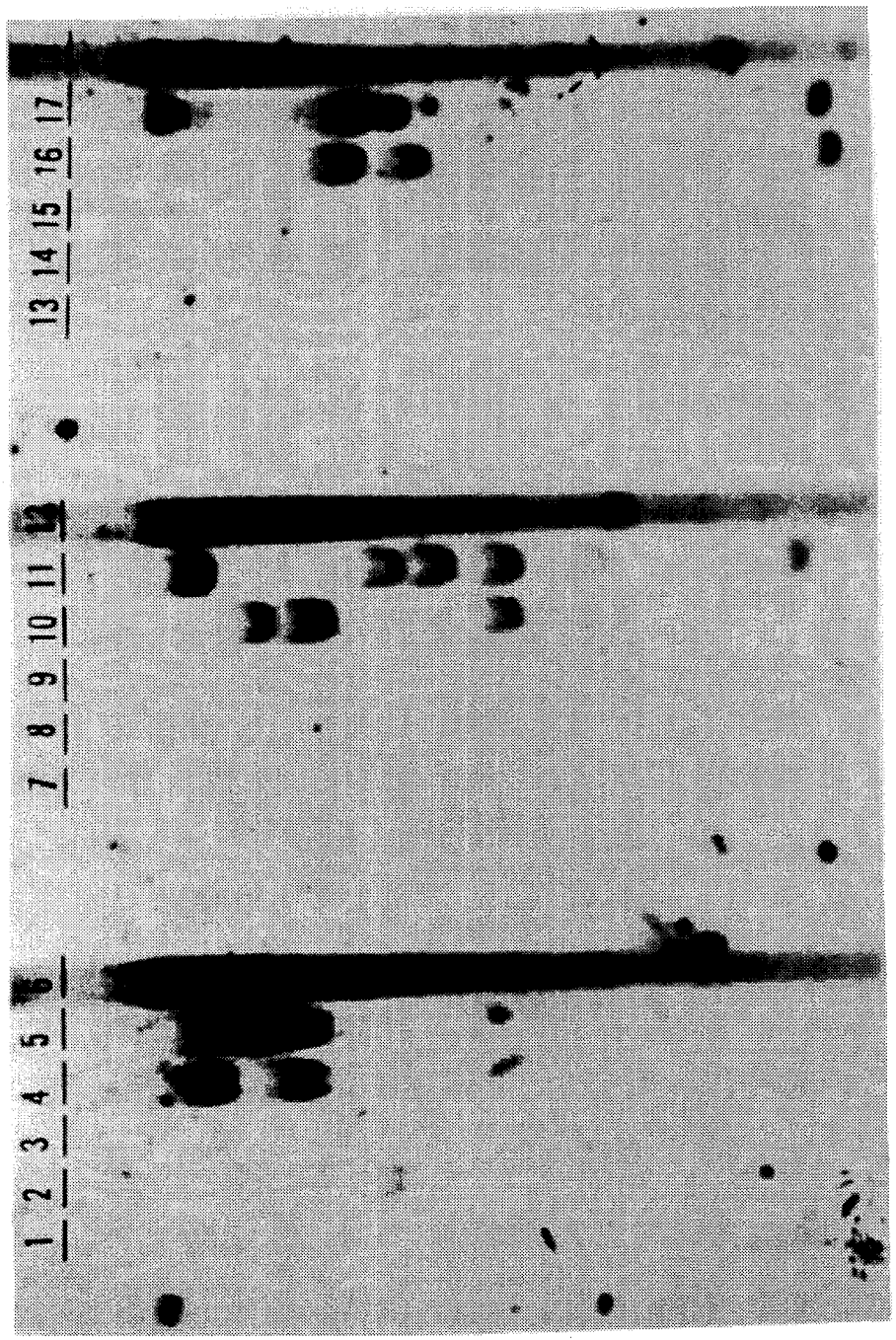

Southern genomic blot analysis: A Southern hybridization of genomic DNA from various species was performed. As shown in FIG. 7A, genomic DNA samples from hamster (lanes 1, 7 and 13), mouse (lanes 2, 8 and 14), rat (lanes 3, 9 and 15), goat (lanes 4, 10 and 16), cattle (lanes 5, 11 and 17) and human (lanes 6, 12 and 18) were digested with EcoRI (lanes 1–6), PstI (lanes 7–12), and XbaI (lanes 13–18). The blot was hybridized with a probe generated by PCR of 46MJ4 using MJ66 and MJ5 and washed in 0.2× SSC/0.1% SDS at 65° C. for 1 hour and exposed for 11 days at −80° C. The same blot was stripped, rehybridized with the same probe and washed in 1×SSC/0.1% SDS at 42° C. for 1 hour and exposed for 10 days at −80° C. (FIG. 7B). As shown in FIG. 7A, Southern hybridization of a zoo blot showed that under high stringency wash, EcoRI digested DNA revealed a single band of 7 kb in goat, two bands of 5 kb and 7.5 kb in bovine, and a band of 3.2 kb in human DNA. With PstI digestion, there were two bands of 3.7 and 5.5 kb in goat, five bands of 1.1, 1.8.2.7, 3.1, and 8 kb in bovine and one band of 1.7 kb in human DNA. XbaI digestion showed a similar pattern with two bands of 2.8 and 3.4 kb in goat, three bands of 3, 3.4, and larger than 10 kb in bovine and one band of 1.9 kb in human DNA. No obvious bands were observed in DNA from rat, mouse, and Chinese hamster. However, as shown in FIG. 7B, when the filter was washed at 42° C. in a solution containing 1×SSC/ 0.1% SDS, a smear background in human DNA was found and an additional band appeared in caprine and bovine DNA. Under the low stringency wash, some faint bands could be seen in lanes containing DNAs of rat, mouse, and hamster.

To determine the human chromosomal location of β-mannosidase, a panel of 24 human/rodent hybrids was studied. Approximately 15 μg of PstI digested genomic DNA from 24 human/rodent somatic cell hybrids each containing a single human chromosome indicated by lane number, were hybridized with a cDNA probe generated by PCR of plasmid DNA of clone 46MJ4 using primers MJ66 and MJ5. The hybridized blot was washed in 1×SSC/0.1 SDS for 1 hour at 42° C. and exposed at −80° C. for 10 days. The results are shown in FIG. 8, wherein the number on top represents the human chromosome retained in that somatic cell line, H represents human control DNA, M represents mouse control DNA, C represents Chinese hamster control DNA and S represents DNA molecular marker III. Southern hybridization of PstI cleaved DNAs revealed a 1.7 kb-band in the hybrid NA10115 (See FIG. 8, lane 4) using a PCR product from the coding region of 46MJ4 as a probe. Its human origin was demonstrated by the observation of a band with the same size in the control human DNA. Ninety-seven percent of cells from the hybrid NA10115 contain chromosome 4. Two bands of larger size were also found in several other hybrids, most likely due to incomplete restriction digestion. Like the zoo blot, the human control showed a smear background. Similar results were obtained using other bovine β-mannosidase cDNA probes (data not shown).

Discussion

The composite β-mannosidase cDNA of the present invention contains 3852 base pairs consisting of a 74 base pair 5' non-coding region, followed by a 2637 base pair coding region encoding 879 amino acids, followed by a 1141 base pair 3' non-coding region and finally a 13 base pair poly (A) tail. The first in-frame ATG codon is flanked by a sequence in good agreement with the consensus sequence for eukaryotic initiation codons (Kozak, M. *Cell* 44:283–292 (1986)) and followed by 17 amino acids containing the characteristic features of a signal peptide sequence. von Heijne, *G. Nucleic Acids Res.* 14:4683–4690 (1986). It is therefore presumed that the first in frame ATG is the initiation codon for β-mannosidase protein. Since the β-mannosidase protein was blocked at the N-terminus, the precise cleavage site of the mature protein is unknown. However, based on the (−3, −1) rule, (von Heijne, *G. Nucleic Acids Res.* 14:4683–4690 (1986)) it is predicted that the signal peptide is cleaved after residue 17 (A).

Figure 9:
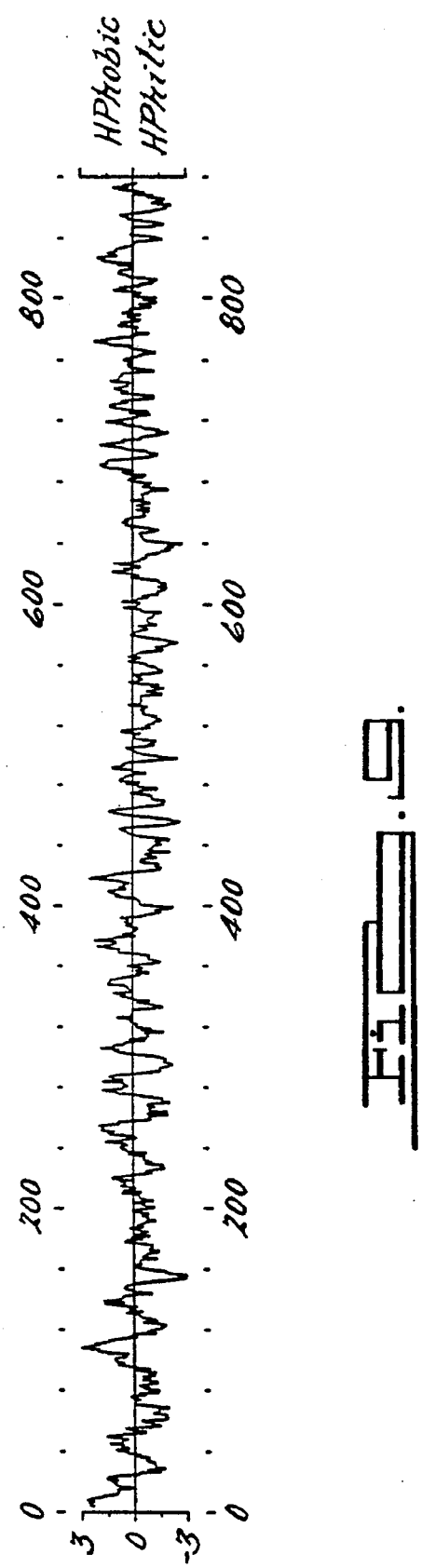
FIG. 9 is a hydropathy plot of the β-mannosidase polypeptide predicted from the full-length cDNA.

As shown in FIG. 9, besides the signal peptide sequence, several hydrophobic regions (e.g. amino acid residues 96 to 114 and 406 to 422) are predicted according to Kyte and Doolitte (Kyte, J. et al., *J. Mol Biol.* 157:105–132 (1982)) (window size 7), however, none of them is likely to be a membrane spanning peptide. The hydropathy profile of the β-mannosidase polypeptide shows dispersed hydrophobic or hydrophilic regions except around amino acids 490 to 640 which is mainly hydrophilic.

Clones 46MJ4, r2, and 47MJ4 contained different 3' regions (see FIG. 3). The 3' non-coding region of clone r8 probably represents the true sequence for β-mannosidase cDNA since its sequence was found in clones 46MJ4 (only missing the final 20 bp) and r2 (except for the final 106 bp). The terminal sequences of the 3' non-coding regions of clone #47MJ4 (approximately 450 bp) and r2 (approximately 1 kb) were not found in other clones and are most likely to be cloning artifacts. Two possible poly (A) signal sequences (AATATA and ATTATA) were found in both 46MJ4 and r8 clones at 32 bases and 14 bases before the poly (A) tail. Various non-consensus poly (A) signal sequences have been reported in several lysosomal enzymes and other mammalian genes. Stein, C. et al., *J. Biol. Chem.* 264:1252–1259 (1989); Stoltzfus, L. J. et al., *J. Biol. Chem.* 267:6570–6575 (1992) and Lin, B. et al., *Hum. Mol. Genet.* 2:1541–1545 (1993).

The deduced peptide sequence from the cDNA matches all peptide sequences obtained from purified β-mannosidase, including those containing incomplete or mixed sequences. There are four discrepancies between the microsequenced amino acid sequences from CNBr/tryptic peptides and those predicted from the cDNA. Two (686 and 864) occur at positions with uncertain residue assignments in peptide sequences and thus are most likely due to peptide sequencing artifacts. The other two (65 and 709) may reflect natural polymorphisms.

Deglycosylation studies (Sopher, B. L. et al., *Biochem. J.* 289:343–347 (1993)) suggested that bovine β-mannosidase may contain seven to nine complex type oligosaccharides. Only six potential glycosylation sites are present at amino acid residues 35–37, 77–79, 297–299, 302–304, 607–609, and 803–805. This difference might be due to an overestimation of protein size by SDS-PAGE, since attached carbohydrate can distort mobility. Mahuran, D. J. et al., *J. Biol. Chem.* 263:4612–4618 (1988).

As stated above, the 2637 base pair coding region encodes 879 amino acids. This would give a predicted molecular mass of approximately 103 kDa. Lysosomal enzymes usually undergo limited proteolytic processing including trimming the N-terminal or C-terminal sequences, or cleaving internal peptides. An interesting feature of the cDNA of the present invention is that a peptide sequence (171) is located immediately adjacent to the stop codon. If this peptide were derived from both 100 and 110 kDa proteins, then β-mannosidase does not undergo C-terminal processing in kidney lysosomes. The region from amino acid residue 490 to residue 610 appears to be mainly hydrophilic and might be susceptible to proteolytic cleavage. With the full-length cDNA of the present invention, expression and pulse chase studies are performed to determine the biosynthesis and processing of β-mannosidase and the relationship between the β-mannosidase peptides observed during the protein preparation.

A single transcript of approximately 4.2 kb was revealed in both normal and β-mannosidosis animals and in both bovine and caprine tissues. The size difference observed between the cloned cDNA sequences of β-mannosidase (3.85 kb) and the RNA transcript (4.2 kb) presumably reflects some missing 5' non-coding region and the poly A tail. The high GC content in the 5' region may hinder reverse transcription in the 5' RACE. The size of the transcripts was identical in goats and cattle as predicted by the observation that these ruminants had identical β-mannosidase peptide sizes after deglycosylation. Sopher, B. L. et al., *J. Biol. Chem.* 267:6178–6182 (1992) and Sopher, B. L. et al., *Biochem. J.* 289:343–347 (1993).

No size difference was revealed between normal mRNA and β-mannosidosis mRNA. However, the mRNA level in affected goats and calves was much lower compared to controls after standardizing the RNA loading with GAPDH. The observation of reduced levels of normal sized mRNA in β-mannosidosis animals implies that the β-mannosidosis in ruminants is most likely to be caused by point mutations or small deletions producing a premature stop codon (Cheng, J. et al., *Mol. Cell. Biol.* 13:1892–1902 (1993); Mahuran, D. J. *Biochim. Biophys. Acta Mol. Basis Dis.* 1096:87–94 (1991); Zhang, Z. -X. et al., *Hum. Mol. Genet.* 3:139–145 (1994) and O'Dowd, B. F. et al., *Proc. Natl. Acad. Sci. USA* 82:1184–1188 (1985)) or mutations in the promoter region affecting the transcription initiation. Southern analysis with several restriction enzyme digestion revealed no gross gene rearrangements in affected and carrier β-mannosidosis animals. The hybridization of restriction enzyme digested genomic DNA with a cDNA fragment of bovine β-mannosidase revealed 2–6 bands of approximately 1 to 10 kb in the bovine species, two bands of approximately 2.8 to 7 kb in the caprine species, and a single band in humans. This result suggests that cattle may contain a large genomic structure with larger introns, pseudogenes, or gene families. The genomic structure of human β-mannosidase appears to be relatively small and not complex.

Homology searches against GenBank revealed no significant homologies between β-mannosidase and other lysosomal enzymes. However, some unexpected homology between a human expressed sequence tag (EST01397) for an unknown gene (Adams, M. D. et al., *Nature* 355:632–634 (1992)) was observed. There was 80% identity in a 454 base pair overlap, from nucleotide 1720 to 2162 in the bovine cDNA, spanning the second EcoRI site. Some homology at the amino acid level was observed mostly in the central region of this human cDNA. The open reading frame in the human sequence is shifted by insertion of nucleotides at several positions, presumably due to sequence errors in regions containing G stretches.

β-Mannosidase had not previously been cloned from any species and there are three lines of evidence to support the authenticity of the β-mannosidase cDNA of the present invention. First, the deduced amino acid sequence from the nucleotide sequence of the cDNA is colinear with all β-mannosidase peptide sequences (more than 104 residues) determined by direct amino acid sequencing. Second, the location of the cDNA is on human chromosome 4, in agreement with previous reports. Fisher, R. A. et al., *Am. J. Hum. Genet.* 41:A165 (1987) and Lundin, L. -G., *Biochem. Genet.* 25:603–610 (1987). Third, the transcript of the cDNA in affected β-mannosidosis animals is much lower than in normal animals.

SPECIFIC EXAMPLE 2

A bovine β-mannosidosis carrier test is provided which can quickly determine bovine β-mannosidosis carders from blood or tissue samples using a technique known as AIRS (artificial introduction of restriction sites). It involves PCR amplification of a 187 base pair segment of genomic DNA surrounding the point mutation site, selectively creating a BstNI restriction site on the normal ampiicon and leaving the mutant ampiicon without such a site. This restriction site, which is not present in the normal cDNA sequence, was created in the normal ampiicon with an intentional single base mismatch in the PCR sense primer. That one base change placed in the normal sequence forms the BstNI restriction site (recognition sequence: $CC^A/_TGG$). The following primers were used:

Sense Primer MJ-124: 5' ACTGTATTCTTTTACCCCTG 3' SEQ ID NO. 3

Antisense Primer MJ-125: 5' AAGTGGCTAACGAGACACCT 3' SEQ ID NO. 4

Primer MJ-124 is a 20 base PCR primer that corresponds to bases 2,554 to 2,573 of the bovine β-mannosidase cDNA sequence. It differs from the actual sequence by one nucleotide, C as opposed to T, at position 2,571. The primer's 3' end is immediately prior to the mutation site.

Primer MJ-125 is a 20 base PCR primer that corresponds to the complement of bases 2,721 to 2,740 of the bovine β-mannosidase cDNA sequence. It differs from the actual sequence by one nucleotide, G as opposed to C, at position 2,729. This nucleotide change was made to avoid possible primer-dimer formation that could prove deleterious in some cases and thus, the change is not central to the test itself.

Materials and Methods

Blood DNA Prep for PCR: A) Premade Solutions—All solutions should be made with great care to avoid ampiicon contamination. PCR dedicated pipetors and aerosol resistant tips were used. RBC Lysis Buffer (stored at 4°) was made with 155 mM NH₄Cl, 10 mM NaHCO₃, 0.1 mM EDTA, pH 7.4 at 4°. For 1 liter, 8.29 g NH₄Cl, 0.84 g NaHCO₃, and 200 µl 500 mM EDTA was used (adjust pH with 10N NaOH).

B) Protocols—All operations were performed on ice unless otherwise noted. Aerosol resistant tips and PCR dedicated pipetors were used to avoid ampiicon contamination. Blood was collected in sodium heparin Vacutainer tubes (green caps, Becton Dickinson). They can be stored for up to 10 days or more at 4° C. To a 1.5 ml microcentrifuge tube 0.5 ml of ice cold RBC Lysis Buffer was added. 100 µl blood was added and mixed by pipeting up and down several times. This was left on ice for 10 min or more. The solution should go from an opaque red to a translucent red. The tubes were then spun in a microcentrifuge at top speed for 30 sec. There should be a small but clearly visible pellet of white cells and on top of it a fairly loose pellet of red cell debris (this is sometimes difficult to see against the red supernatant). The red pellet was resuspended by very gently pipeting the supernatant up and down. Care was taken not to dislodge the relatively firm white cell pellet. As much suspension as possible was removed. To the white cell pellet 100 µl 50 mM NaOH was added and resuspend by vigorously pipetting in an out several times. The tubes were then put in a boiling H₂O bath for 10 min and then put on ice. A 5 µl 2M Tris-HCl, pH 8.0 was added to neutralize. A 5 µl aliquot was used as a template in a typical PCR.

PCR Procedures: A)Premade Solutions—Ampiicon contamination was avoided and store premade solutions stored in small aliquots at −20° C. 10×PCR Buffer was made with 500 mM KCI and 100 mM Tris-HCl, pH 8.3.

B) Protocols—Each PCR had 20 µl total volume comprised of 5 µl genomic DNA preparation and 15 µl reagent cocktail. The components of the cocktail were mixed in bulk sufficiently large enough to accommodate all the samples to be tested that day. For each PCR, the cocktail contained 2.0 µl 10×PCR Buffer, 1.6 µl 25 mM MgCl₂, 1.6 µl dNTPs (dATP, dCTP, dGTP, dTTP), 2.5 mM each, 0.5 µl 20 µM Sense Primer MJ-124, 0.5 µl 20 µM Antisense Primer MJ-125, 0.1 µl 5 Units/µl AmpliTaq DNA Polymerase (Perkin Elmer) and 8.7 µl H₂O. For each PCR, 15 µl of the cocktail was put into a MicroAmp* Reaction Tube with Cap (Perkin Elmer), followed by 5 µl of the appropriate genomic DNA preparation. Every time PCR was performed a negative control reaction, containing 15 µl cocktail and 5 µl H₂O, was also run. The tubes are capped and put into a Gene-Amp™ PCR System 9600 (Perkin Elmer). The thermal cycling profile is as follows:

|  | 7 min. at 94° C. | Initial DNA Denaturation |
| --- | --- | --- |
| 35 Cycles | 94° for 30 sec. | DNA Denaturation |
|  | 55° for 30 sec. | Primer Annealing |
|  | 72° for 30 sec. | Primer Extension |
|  | 10 min. at 72° C. | Final Elongation |
|  | Hold at 4° C. |  |

BstNI Restriction Digest of Amplicons: After the thermal cycling was complete, the PCR tubes were removed from the thermal cycler and taken to another location for post-PCR manipulation to avoid contamination of the pre-PCR work area. To each 20 µl PCR tube, 0.5 µl of 10 units/µl BstNI (New England Biolabs, Inc.) was added. The tubes were then incubated at 60° C. for 2 hours.

Agarose Gel Electrophoresis of BstNI Digested Ampiicons: Four µl of electrophoresis loading buffer (30% glycerol, 0.01% bromophenol blue, 0.01% xylene cyanol) was added to each reaction tube. A 12 µl aliquot of each mixture was applied to a 4% agarose gel containing 0.5×TBE buffer (89 mM Tris-borate, 89 mM boric acid, 2 mM EDTA) and 1 µl/ml ethidium bromide and submerged in chamber buffer with the same components. DNA molecular weight maker V (pBR322 DNA digested with HaeIII, Boehdnger Mannheim Biochemcials) was also prepared for the gel. The gel was run at 100 to 150 volts for between 40 minutes and 2 hours depending on the gel size. DNA fragments were visualized on a UV light box ($\lambda$=302 nm).

Results

FIG. 10 shows the sequence of the normal β-mannosidase ampiicon with the introduced nucleotide changes. A small segment of the mutant β-mannosidase amplicon is shown below the first line. The mutation, which is underlined, abolishes the BstNI site that was introduced in the normal ampiicon. A natural BstNI site found in both the normal and mutant alleles served as an internal control for the completeness of the BstNI digestion. In a normal animal this amplification and digestion results in DNA fragments of 125, 43 and 19 base pairs. In a carrier animal, which has one copy of the normal gene and one copy of the mutant gene, the DNA fragments are 144, 125, 43 and 19 base pairs. The DNA fragments were separated and visualized by electrophoresis on a 4% agarose gel paying attention to the presence or absence of the 144 base pair band.

Figure 11:
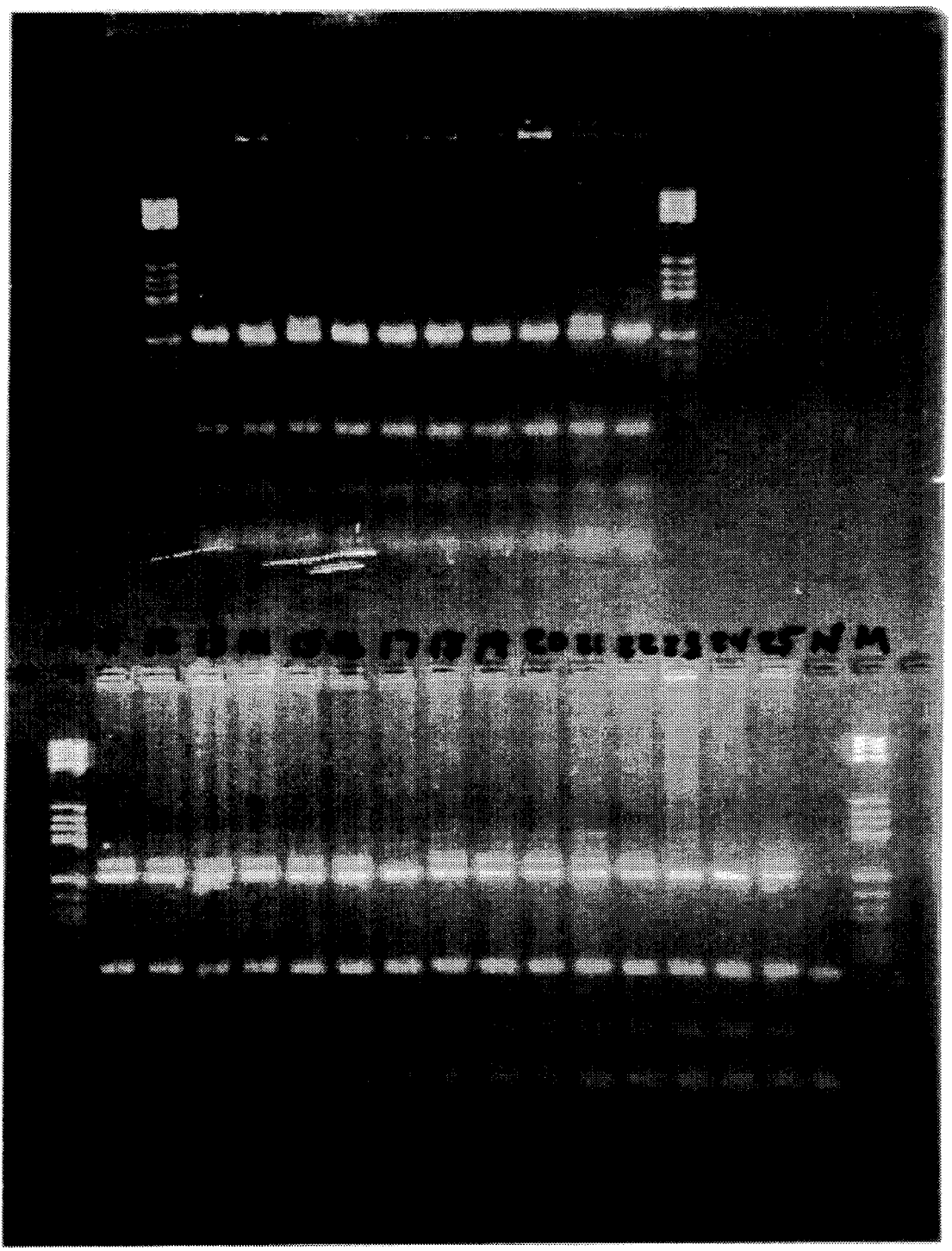
FIG. 11 is a photograph of a gel showing the results of the bovine β-mannosidosis carrier test for twenty-five animals.

FIG. 11 shows a gel with test results from 25 animals. Animals 3, 9, 11–16, 18–22 and 25 are β-mannosidosis carriers. In FIG. 11, lanes marked M are molecular weight markers and the lane marked N is a negative control. Animals 1, 2, 4–8, 10, 17, 23 and 24 are normal.

Discussion

The above-described carrier test can quickly determine bovine β-mannosidosis carriers from blood or tissue samples. However, it will be appreciated to those skilled in the art that the above method is merely exemplary of the many carrier test methods which may be performed in accordance with the present invention.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All references cited herein are expressly incorporated by reference.

We claim:

1. An isolated and purified oligonucleotide sequence consisting of at least twenty contiguous nucleic acids of the nucleotide sequence of SEQ ID NO. 1 which specifically hybridizes with the bovine β-mannosidase gene.

2. An isolated and purified oligonucleotide sequence consisting of at least twenty contiguous nucleic acids of the nucleotide sequence that is complementary to the sequence of SEQ ID NO. 1 which specifically hybridizes with the bovine β-mannosidase gene.

3. A method of detecting a bovine β-mannosidase gene in a sample comprising the steps of:

a) contacting the sample with an oligonucleotide comprising at least twenty contiguous nucleic acids of the nucleotide sequence of SEQ ID NO. 1 under conditions favorable for hybridization of the oligonucleotide to any complementary sequences of nucleic acid in the sample; and b) detecting hybridization, thereby detecting a bovine β-mannosidase gene.

4. The method of claim 3, further comprising the step of:

c) quantifying hybridization of the oligonucleotide to complementary sequences.

5. The method of claim 3, wherein in SEQ ID No. 1, the adenine nucleotide at position 2,648 is replaced with a guanine nucleotide.

6. An assay kit for screening for a bovine β-mannosidase gene comprising:

a) an oligonucleotide comprising at least twenty contiguous nucleic acids of the nucleotide sequence of SEQ ID NO. 1 which specifically hybridizes with the bovine β-mannosidase gene;

b) reagents for hybridization of the oligonucleotide to a complementary nucleic acid sequence; and c) container means for a)–b).

7. A method of detecting a bovine β-mannosidase gene in a sample comprising the steps of:

a) contacting the sample with an oligonucleotide comprising at least twenty contiguous nucleic acids of the nucleotide sequence that is complementary to the sequence of SEQ ID NO. 1 under conditions favorable to hybridization of the oligonucleotide to any complementary sequences of nucleic acid in the sample; and b) detecting hybridization, thereby detecting a bovine β-mannosidase gene.

8. The method of claim 7, further comprising the step of:

c) quantifying hybridization of the oligonucleotide to complementary sequences.

9. The method of claim 7, wherein in SEQ ID No. 1, the adenine nucleotide at position 2,648 is replaced with a guanine nucleotide.

10. An assay kit for screening for a bovine β-mannosidase gene comprising:

a) an oligonucleotide comprising at least twenty contiguous nucleic acids from the nucleotide sequence that is complementary to the sequence of SEQ ID NO. 1 which specifically hybridizes with the bovine β-mannosidase gene;

b) reagents for hybridization of the oligonucleotide to a complementary nucleic acid sequence; and c) container means for a)–b).

11. The assay kit of claim 10, wherein in SEQ ID No. 1, the adenine nucleotide at position 2,648 is replaced with a guanine nucleotide.

12. A method for detecting a mutated β-mannosidase gene in a bovine comprising the steps of:

a) amplifying a DNA sample from the bovine by polymerase chain reaction to produce polymerase chain reaction products, wherein the polymerase chain reaction uses wherein the primers are selected from the group consisting of SEQ ID NOS: 3 and 4;

b) digesting the polymerase chain reaction products with a restriction enzyme specific to the restriction site of the restriction site primer to produce DNA fragments; and c) detecting the DNA fragments, thereby detecting a mutated bovine β-mannosidase gene.

13. The method of claim 12, wherein the restriction enzyme is BstNI.

14. The method of claim 12, wherein the DNA fragments are detected by gel electrophoresis.

15. An oligonucleotide probe capable of detecting a mutation associated with bovine β-mannosidosis wherein the mutation is a nucleotide change at position 2,648 of the bovine β-mannosidase gene.

* * * * *

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
    ( A ) LENGTH: 3852 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: CDS
    ( B ) LOCATION: 75..2711

( x i ) SEQUENCE DESCRIPTION: SEQ ID NO:1:

```
CTCAGGCCGA  GCGTGGCTTC  CGCTGCCCAC  CGCATCCCTC  GGGTTCTTGC  CCTGTGCGGG                60

TACCGGGCAA  CACC ATG CTC CTC CGC CTG CTC CTG CTG CTT GCG CCG TGC                     110
              Met Leu Leu Arg Leu Leu Leu Leu Leu Ala Pro Cys
               1               5                        10

GGT GCG GGC TTC GCT ACC AAG GTG GTC AGC ATC AGT TTG CGG GGA AAC                      158
Gly Ala Gly Phe Ala Thr Lys Val Val Ser Ile Ser Leu Arg Gly Asn
         15                  20                  25

TGG AAG ATC CAC AGC GGG AAC GGT TCG CTG CAG CTG CCC GCG ACG GTT                      206
Trp Lys Ile His Ser Gly Asn Gly Ser Leu Gln Leu Pro Ala Thr Val
         30                  35                  40

CCC GGT TGC GTG CAC AGC GCC TTG TTC AAC AAG AGG ATC ATC AAG GAT                      254
Pro Gly Cys Val His Ser Ala Leu Phe Asn Lys Arg Ile Ile Lys Asp
 45                  50                  55                  60

CCT TAC TAC AGA TTT AAT AAC CTT GAC TAT AGA TGG ATA GCC TTG GAT                      302
Pro Tyr Tyr Arg Phe Asn Asn Leu Asp Tyr Arg Trp Ile Ala Leu Asp
                 65                  70                  75

AAC TGG ACC TAT ATC AAG AAA TTT AAA CTC CAC TCT GAT ATG AGC ACA                      350
Asn Trp Thr Tyr Ile Lys Lys Phe Lys Leu His Ser Asp Met Ser Thr
             80                  85                  90

TGG AGT AAA GTA AAT TTG GTT TTT GAG GGT ATC GAT ACA GTT GCA GTA                      398
Trp Ser Lys Val Asn Leu Val Phe Glu Gly Ile Asp Thr Val Ala Val
         95                 100                 105

GTC CTG CTC AAC AGT GTT CCC ATT GGC AAA ACA GAC AAC ATG TTC AGA                      446
Val Leu Leu Asn Ser Val Pro Ile Gly Lys Thr Asp Asn Met Phe Arg
    110                 115                 120

AGA TAC AGC TTT GAT ATT ACA CAT ACG GTC AAA GCA GTG AAC ATC ATT                      494
Arg Tyr Ser Phe Asp Ile Thr His Thr Val Lys Ala Val Asn Ile Ile
125                 130                 135                 140

GAG GTG CGT TTC CAG TCA CCA GTG GTA TAT GCG AAC CAG AGG AGC GAA                      542
Glu Val Arg Phe Gln Ser Pro Val Val Tyr Ala Asn Gln Arg Ser Glu
                145                 150                 155

CGT CAC ACT GCC TAC TGG GTG CCC CCC AAC TGC CCT CCA CCT GTG CAG                      590
Arg His Thr Ala Tyr Trp Val Pro Pro Asn Cys Pro Pro Pro Val Gln
            160                 165                 170

GAT GGC GAA TGT CAT GTC AAC TTT ATT CGC AAG ATG CAG TGT TCC TTT                      638
Asp Gly Glu Cys His Val Asn Phe Ile Arg Lys Met Gln Cys Ser Phe
        175                 180                 185

GGA TGG GAC TGG GGA CCT TCT TTT CCT ACC CAG GGC ATC TGG AAA GAT                      686
Gly Trp Asp Trp Gly Pro Ser Phe Pro Thr Gln Gly Ile Trp Lys Asp
    190                 195                 200
```

| | | | | | | | | | | | | | | | | |
|---|---|---|---|---|---|---|---|---|---|---|---|---|---|---|---|---|
| GTT | AGA | ATT | GAA | GCC | TAT | AAT | GTT | TGT | CAT | CTG | AAC | TAC | TTC | ATG | TTT | 734 |
| Val | Arg | Ile | Glu | Ala | Tyr | Asn | Val | Cys | His | Leu | Asn | Tyr | Phe | Met | Phe | |
| 205 | | | | 210 | | | | | 215 | | | | | 220 | | |
| ACC | CCC | ATC | TAC | GAT | AAC | TAT | ATG | AAG | ACA | TGG | AAT | CTT | AAA | ATA | GAG | 782 |
| Thr | Pro | Ile | Tyr | Asp | Asn | Tyr | Met | Lys | Thr | Trp | Asn | Leu | Lys | Ile | Glu | |
| | | | | 225 | | | | 230 | | | | | 235 | | | |
| TCG | TCT | TTT | GAT | GTT | GTC | AGT | TCA | AAG | CTG | GTT | TCT | GGT | GAA | GCA | ATT | 830 |
| Ser | Ser | Phe | Asp | Val | Val | Ser | Ser | Lys | Leu | Val | Ser | Gly | Glu | Ala | Ile | |
| | | | 240 | | | | | 245 | | | | | 250 | | | |
| GTA | GCC | ATC | CCT | GAA | CTA | AAC | ATA | CAG | CAG | ACA | AAC | AAC | ATT | GAA | CTT | 878 |
| Val | Ala | Ile | Pro | Glu | Leu | Asn | Ile | Gln | Gln | Thr | Asn | Asn | Ile | Glu | Leu | |
| | | 255 | | | | | 260 | | | | | 265 | | | | |
| CAA | CAT | GGG | GAA | AGG | ACT | GTT | GAG | CTC | TTT | GTG | AAA | ATC | GAC | AAG | GCT | 926 |
| Gln | His | Gly | Glu | Arg | Thr | Val | Glu | Leu | Phe | Val | Lys | Ile | Asp | Lys | Ala | |
| | 270 | | | | | 275 | | | | | 280 | | | | | |
| ATT | ATT | GTA | GAA | ACT | TGG | TGG | CCT | CAT | GGA | CAT | GGA | AAC | CAG | ACT | GGG | 974 |
| Ile | Ile | Val | Glu | Thr | Trp | Trp | Pro | His | Gly | His | Gly | Asn | Gln | Thr | Gly | |
| 285 | | | | 290 | | | | | 295 | | | | | 300 | | |
| TAC | AAC | ATG | AGC | GTT | ATT | TTT | GAG | CTG | GAT | GGA | GGC | TTA | CGT | TTT | GAA | 1022 |
| Tyr | Asn | Met | Ser | Val | Ile | Phe | Glu | Leu | Asp | Gly | Gly | Leu | Arg | Phe | Glu | |
| | | | | 305 | | | | | 310 | | | | | 315 | | |
| AAA | TCA | GCT | AAG | GTT | TAT | TTT | AGG | ACA | GTG | GAA | CTT | GTA | GAA | GAG | CCC | 1070 |
| Lys | Ser | Ala | Lys | Val | Tyr | Phe | Arg | Thr | Val | Glu | Leu | Val | Glu | Glu | Pro | |
| | | | 320 | | | | | 325 | | | | | 330 | | | |
| ATA | CAA | AAT | TCT | CCT | GGT | CTG | AGT | TTC | TAC | TTC | AAA | ATT | AAT | GGA | CTT | 1118 |
| Ile | Gln | Asn | Ser | Pro | Gly | Leu | Ser | Phe | Tyr | Phe | Lys | Ile | Asn | Gly | Leu | |
| | | 335 | | | | | 340 | | | | | 345 | | | | |
| CCC | ATA | TTT | CTG | AAA | GGC | TCG | AAT | TGG | ATC | CCT | GCA | GAT | TCA | TTC | CAG | 1166 |
| Pro | Ile | Phe | Leu | Lys | Gly | Ser | Asn | Trp | Ile | Pro | Ala | Asp | Ser | Phe | Gln | |
| | 350 | | | | | 355 | | | | | 360 | | | | | |
| GAT | AGA | GTA | ACC | TCT | GCC | ATG | TTG | CGG | CTC | CTC | TTG | CAG | TCT | GTT | GTG | 1214 |
| Asp | Arg | Val | Thr | Ser | Ala | Met | Leu | Arg | Leu | Leu | Leu | Gln | Ser | Val | Val | |
| 365 | | | | 370 | | | | | 375 | | | | | 380 | | |
| GAT | GCT | AAC | ATG | AAT | GCT | CTT | CGG | GTC | TGG | GGA | GGA | GGA | GTT | TAT | GAG | 1262 |
| Asp | Ala | Asn | Met | Asn | Ala | Leu | Arg | Val | Trp | Gly | Gly | Gly | Val | Tyr | Glu | |
| | | | | 385 | | | | | 390 | | | | | 395 | | |
| CAG | GAT | GAA | TTC | TAC | GAA | CTC | TGT | GAT | GAA | CTA | GGC | ATA | ATG | ATA | TGG | 1310 |
| Gln | Asp | Glu | Phe | Tyr | Glu | Leu | Cys | Asp | Glu | Leu | Gly | Ile | Met | Ile | Trp | |
| | | | 400 | | | | | 405 | | | | | 410 | | | |
| CAG | GAT | TTC | ATG | TTT | GCC | TGT | GCG | CTT | TAC | CCA | ACC | GAT | AAG | GAT | TTC | 1358 |
| Gln | Asp | Phe | Met | Phe | Ala | Cys | Ala | Leu | Tyr | Pro | Thr | Asp | Lys | Asp | Phe | |
| | | 415 | | | | | 420 | | | | | 425 | | | | |
| ATG | GAT | TCT | GTG | AGA | GAA | GAA | GTC | ACT | CAC | CAG | GTC | CGG | AGA | CTG | AAA | 1406 |
| Met | Asp | Ser | Val | Arg | Glu | Glu | Val | Thr | His | Gln | Val | Arg | Arg | Leu | Lys | |
| | | 430 | | | | | 435 | | | | | 440 | | | | |
| TCT | CAT | CCC | TCC | ATC | ATC | ACA | TGG | AGT | GGG | AAT | AAT | GAA | AAT | GAA | GCA | 1454 |
| Ser | His | Pro | Ser | Ile | Ile | Thr | Trp | Ser | Gly | Asn | Asn | Glu | Asn | Glu | Ala | |
| 445 | | | | 450 | | | | | 455 | | | | | 460 | | |
| GCA | CTA | ATG | ATG | GGT | TGG | TAT | GAT | ACA | AAG | CCT | GGC | TAC | TTG | CAA | ACC | 1502 |
| Ala | Leu | Met | Met | Gly | Trp | Tyr | Asp | Thr | Lys | Pro | Gly | Tyr | Leu | Gln | Thr | |
| | | | | 465 | | | | | 470 | | | | | 475 | | |
| TAC | ATC | AAA | GAC | TAT | GTG | ACA | CTG | TAT | GTG | AAA | AAC | ATC | CGA | ACG | ATC | 1550 |
| Tyr | Ile | Lys | Asp | Tyr | Val | Thr | Leu | Tyr | Val | Lys | Asn | Ile | Arg | Thr | Ile | |
| | | | 480 | | | | | 485 | | | | | 490 | | | |
| GTC | TTA | GAA | GGA | GAC | CAG | ACT | CGT | CCT | TTT | ATC | ACA | TCC | AGT | CCT | ACA | 1598 |
| Val | Leu | Glu | Gly | Asp | Gln | Thr | Arg | Pro | Phe | Ile | Thr | Ser | Ser | Pro | Thr | |
| | | 495 | | | | | 500 | | | | | 505 | | | | |
| AAT | GGG | GCC | AAA | ACC | ATT | GCA | GAA | GGT | TGG | CTC | TCT | CCA | AAC | CCC | TAT | 1646 |
| Asn | Gly | Ala | Lys | Thr | Ile | Ala | Glu | Gly | Trp | Leu | Ser | Pro | Asn | Pro | Tyr | |
| | 510 | | | | | 515 | | | | | 520 | | | | | |

| | | | | | | | | | | | | | | | | |
|---|---|---|---|---|---|---|---|---|---|---|---|---|---|---|---|---|
| GAC | CTG | AAT | TAT | GGG | GAC | GTA | CAT | TTT | TAT | GAT | TAT | GTG | AGT | GAC | TGC | 1694 |
| Asp | Leu | Asn | Tyr | Gly | Asp | Val | His | Phe | Tyr | Asp | Tyr | Val | Ser | Asp | Cys | |
| 525 | | | | 530 | | | | | 535 | | | | | 540 | | |
| TGG | AAT | TGG | AGA | ACT | TTC | CCC | AAA | GCT | CGA | TTT | GTA | TCT | GAG | TAT | GGA | 1742 |
| Trp | Asn | Trp | Arg | Thr | Phe | Pro | Lys | Ala | Arg | Phe | Val | Ser | Glu | Tyr | Gly | |
| | | | 545 | | | | 550 | | | | | 555 | | | | |
| TAT | CAG | TCC | TGG | CCT | TCC | TTC | AGT | ACA | TTA | GAA | AAG | GTT | TCC | TCT | GAA | 1790 |
| Tyr | Gln | Ser | Trp | Pro | Ser | Phe | Ser | Thr | Leu | Glu | Lys | Val | Ser | Ser | Glu | |
| | | | 560 | | | | 565 | | | | | 570 | | | | |
| GAG | GAC | TGG | TCT | TAC | AGA | AGC | AGC | TTT | GCA | CTT | CAT | CGG | CAA | CAT | TTG | 1838 |
| Glu | Asp | Trp | Ser | Tyr | Arg | Ser | Ser | Phe | Ala | Leu | His | Arg | Gln | His | Leu | |
| | | 575 | | | | 580 | | | | | 585 | | | | | |
| ATT | AAC | GGT | AAC | AAT | GAA | ATG | CTT | CAC | CAG | ATT | GAA | CTT | CAC | TTC | AAG | 1886 |
| Ile | Asn | Gly | Asn | Asn | Glu | Met | Leu | His | Gln | Ile | Glu | Leu | His | Phe | Lys | |
| | 590 | | | | 595 | | | | 600 | | | | | | | |
| CTC | CCA | AAC | AGT | ACA | GAT | CAA | CTA | CGC | AGG | TTC | AAA | GAC | ACT | CTT | TAT | 1934 |
| Leu | Pro | Asn | Ser | Thr | Asp | Gln | Leu | Arg | Arg | Phe | Lys | Asp | Thr | Leu | Tyr | |
| 605 | | | | 610 | | | | | 615 | | | | | 620 | | |
| CTT | ACT | CAG | GTG | ATG | CAG | GCC | CAG | TGT | GTC | AAA | ACA | GAA | ACT | GAA | TTC | 1982 |
| Leu | Thr | Gln | Val | Met | Gln | Ala | Gln | Cys | Val | Lys | Thr | Glu | Thr | Glu | Phe | |
| | | | | 625 | | | | | 630 | | | | | 635 | | |
| TAC | CGT | CGC | AGT | CGC | AGC | GAG | ATA | GTG | AAT | GGA | AAA | GGG | CAC | ACC | ATG | 2030 |
| Tyr | Arg | Arg | Ser | Arg | Ser | Glu | Ile | Val | Asn | Gly | Lys | Gly | His | Thr | Met | |
| | | | 640 | | | | | 645 | | | | | 650 | | | |
| GGG | GCG | CTT | TAT | TGG | CAG | CTC | AAT | GAC | ATC | TGG | CAA | GCT | CCT | TCC | TGG | 2078 |
| Gly | Ala | Leu | Tyr | Trp | Gln | Leu | Asn | Asp | Ile | Trp | Gln | Ala | Pro | Ser | Trp | |
| | | 655 | | | | 660 | | | | | 665 | | | | | |
| TCT | TCT | CTA | GAG | TAT | GGA | GGA | AAG | TGG | AAA | ATG | CTT | CAT | TAC | TTT | GCT | 2126 |
| Ser | Ser | Leu | Glu | Tyr | Gly | Gly | Lys | Trp | Lys | Met | Leu | His | Tyr | Phe | Ala | |
| | 670 | | | | 675 | | | | | 680 | | | | | | |
| CGG | CAT | TTC | TTC | GCC | CCC | CTG | TTA | CCG | GTG | GGT | TTT | GAG | GAT | AAA | GAT | 2174 |
| Arg | His | Phe | Phe | Ala | Pro | Leu | Leu | Pro | Val | Gly | Phe | Glu | Asp | Lys | Asp | |
| 685 | | | | 690 | | | | | 695 | | | | | 700 | | |
| ATG | CTT | TTC | ATC | TAT | GGT | GCG | TCA | CAC | CTT | CAC | TCA | GAC | CAG | CAG | ATG | 2222 |
| Met | Leu | Phe | Ile | Tyr | Gly | Ala | Ser | His | Leu | His | Ser | Asp | Gln | Gln | Met | |
| | | | | 705 | | | | 710 | | | | | 715 | | | |
| ATG | CTC | ACT | GTG | AGA | GTC | CAC | ACT | TGG | AGT | TCC | CTG | GAG | CTC | GTA | TGC | 2270 |
| Met | Leu | Thr | Val | Arg | Val | His | Thr | Trp | Ser | Ser | Leu | Glu | Leu | Val | Cys | |
| | | | 720 | | | | | 725 | | | | | 730 | | | |
| TCT | GAG | TCA | ACT | AAC | CCT | TTC | GTG | ATA | AAA | GCT | GGG | GAG | TCT | GTT | CTC | 2318 |
| Ser | Glu | Ser | Thr | Asn | Pro | Phe | Val | Ile | Lys | Ala | Gly | Glu | Ser | Val | Leu | |
| | | 735 | | | | 740 | | | | | 745 | | | | | |
| CTC | TAT | ACT | AAG | CCA | GTG | CCT | GAG | TTG | CTA | AAA | GGA | TGT | CCC | GGA | TGT | 2366 |
| Leu | Tyr | Thr | Lys | Pro | Val | Pro | Glu | Leu | Leu | Lys | Gly | Cys | Pro | Gly | Cys | |
| | 750 | | | | 755 | | | | | 760 | | | | | | |
| ACA | CGA | CAA | AGC | TGT | GTG | GTT | TCC | TTT | TAC | CTG | TCA | ACT | GAC | GGG | GAA | 2414 |
| Thr | Arg | Gln | Ser | Cys | Val | Val | Ser | Phe | Tyr | Leu | Ser | Thr | Asp | Gly | Glu | |
| 765 | | | | 770 | | | | | 775 | | | | | 780 | | |
| CTC | TTG | AGC | CCA | ATC | AAC | TAT | CAC | TTC | CTG | TCC | TCA | CTG | AAG | AAT | GCC | 2462 |
| Leu | Leu | Ser | Pro | Ile | Asn | Tyr | His | Phe | Leu | Ser | Ser | Leu | Lys | Asn | Ala | |
| | | | | 785 | | | | 790 | | | | | 795 | | | |
| AAG | GGG | CTC | CAC | AAG | GCA | AAT | ATC | ACT | GCC | ACC | ATC | TCG | CAG | CAA | GGG | 2510 |
| Lys | Gly | Leu | His | Lys | Ala | Asn | Ile | Thr | Ala | Thr | Ile | Ser | Gln | Gln | Gly | |
| | | | 800 | | | | 805 | | | | | 810 | | | | |
| GAC | ACA | TTT | GTT | TTT | GAT | CTG | AAA | ACC | TCA | GCT | GTC | GCT | CCC | TTT | GTT | 2558 |
| Asp | Thr | Phe | Val | Phe | Asp | Leu | Lys | Thr | Ser | Ala | Val | Ala | Pro | Phe | Val | |
| | | 815 | | | | 820 | | | | | 825 | | | | | |
| TGG | TTG | GAT | GTA | GGA | AGC | ATC | CCA | GGG | AGA | TTC | AGT | GAC | AAT | GGT | TTC | 2606 |
| Trp | Leu | Asp | Val | Gly | Ser | Ile | Pro | Gly | Arg | Phe | Ser | Asp | Asn | Gly | Phe | |
| | 830 | | | | 835 | | | | | 840 | | | | | | |

| CTC | ATG | ACT | GAG | AAG | ACA | CGG | ACT | GTA | TTC | TTT | TAC | CCT | TGG | AAA | CCC | 2654 |
| Leu | Met | Thr | Glu | Lys | Thr | Arg | Thr | Val | Phe | Phe | Tyr | Pro | Trp | Lys | Pro | |
| 845 | | | | | 850 | | | | | 855 | | | | | 860 | |

| ACC | AGC | AAG | AGT | GAA | TTG | GAG | CAA | TCT | TTT | CAT | GTG | ACT | TCA | CTG | GCT | 2702 |
| Thr | Ser | Lys | Ser | Glu | Leu | Glu | Gln | Ser | Phe | His | Val | Thr | Ser | Leu | Ala | |
| | | | | 865 | | | | | 870 | | | | | 875 | | |

| GAT | ACT | TAC | TGAGGGAATC | AGGTTGTATT | TTCGAGAGCT | GAAGGCAACT | 2751 |
| Asp | Thr | Tyr | | | | | |

| AGAAACAAGT | TGAAGAAGCC | AGGAAATGCA | TCTGCTTGCT | GTCAGGTGTC | TGGTTAGCCA | 2811 |
| CTTGGTTCTC | CCAGGGAAGG | CTGTGTATAT | TCAGGTGATG | TTCTCAACAA | AGCGGTGCCT | 2871 |
| GGGTGCTGTT | CCGTCTGCAC | CAGGGCTGTG | TCTTTAGCTC | TTCCTTTTGC | ACCTTTTGCA | 2931 |
| CCACGTGAAT | CAGTTCTAAC | CCAACTGTCT | CTCCTACCCC | CAAAGGAGGT | CCTGTCCACA | 2991 |
| CGCAGTCCTT | TAAGGGAATC | ACAGGAACAT | GACCAAGTAG | CCCTTTAAGA | GAATTACAGG | 3051 |
| CACACTCCCA | GGTAGCCCTT | AAGGGAATCA | CAGTAATGAC | CATTGTGGTA | TCTGTGGAAT | 3111 |
| CAAATGTGGA | AGATTGTGAG | GGCATGTAGG | CCCCTCAGGA | TAGCTTTGAG | AAATACCAAA | 3171 |
| CGATTGAAAT | GAAACTGCTT | TGTCATTATT | TCCAGAGGAA | ATAGAGATTC | AGATGTTGCA | 3231 |
| ACAGAAAGAG | ATGTCTGGGT | GGTAGCCATA | TTGGTTGTTG | ATGCTGGAAA | GTTTGGTGGG | 3291 |
| ATTGATTATT | GCCATTCGAT | TACTTTTTGA | GTAGGAGTCT | TTTTTCATTT | GTGATTTTTT | 3351 |
| TTTTTAATAA | AATATTTGTT | TTAACAATAA | TAATTTATTT | TTTCAAAGGC | AATTAGTGAT | 3411 |
| TCTTCTTTGG | GAAAAAAAAA | ACTCACATTG | GAATGGACAT | CACCTTGATC | ATGTTGGAAA | 3471 |
| CTTTTGGGTG | TCCTGACGTA | AGTGGTCACC | TGTATTAAGT | ATGGGCTTCA | GATTTGGTTA | 3531 |
| AGTCCAGTGA | ACTTCCAGT | TCAAGACTAT | GGTTTGATTT | GCATGTGATG | AGCCTGGCAG | 3591 |
| CAAAGTGGTA | TTGCCTTTAA | CTTGAGATTG | AACCATTTTA | AAAACACTG | ATTAATTATA | 3651 |
| ATTGCTATGA | AATCATTTTG | TTCTCATCAT | CCTGTTTATA | AAATTACATT | GATAGTGAAG | 3711 |
| CAAGGGGCAA | AATGTTAATA | AGTAGTCAAT | TTGAGTAAAG | GTGTATAGGA | ATATTTTGT | 3771 |
| TCTGCTTGAG | CAACTTTTCT | GTAAGTTTGA | AATATATAAA | AATTTAAGAT | TATATAAATT | 3831 |
| GCATTGACAA | AAAAAAAAA | A | | | | 3852 |

( 2 ) INFORMATION FOR SEQ ID NO:2:

( i ) SEQUENCE CHARACTERISTICS:
        ( A ) LENGTH: 879 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Leu | Leu | Arg | Leu | Leu | Leu | Leu | Ala | Pro | Cys | Gly | Ala | Gly | Phe |
|---|---|---|---|---|---|---|---|---|---|---|---|---|---|---|
| 1 | | | | 5 | | | | | 10 | | | | | 15 |

| Ala | Thr | Lys | Val | Val | Ser | Ile | Ser | Leu | Arg | Gly | Asn | Trp | Lys | Ile | His |
| | | | 20 | | | | | 25 | | | | | 30 | | |

| Ser | Gly | Asn | Gly | Ser | Leu | Gln | Leu | Pro | Ala | Thr | Val | Pro | Gly | Cys | Val |
| | | | 35 | | | | | 40 | | | | | 45 | | |

| His | Ser | Ala | Leu | Phe | Asn | Lys | Arg | Ile | Ile | Lys | Asp | Pro | Tyr | Tyr | Arg |
| | | 50 | | | | | 55 | | | | | 60 | | | |

| Phe | Asn | Asn | Leu | Asp | Tyr | Arg | Trp | Ile | Ala | Leu | Asp | Asn | Trp | Thr | Tyr |
| 65 | | | | | 70 | | | | | 75 | | | | | 80 |

| Ile | Lys | Lys | Phe | Lys | Leu | His | Ser | Asp | Met | Ser | Thr | Trp | Ser | Lys | Val |
| | | | | 85 | | | | | 90 | | | | | 95 | |

```
Asn  Leu  Val  Phe  Glu  Gly  Ile  Asp  Thr  Val  Ala  Val  Val  Leu  Leu  Asn
               100                      105                      110
Ser  Val  Pro  Ile  Gly  Lys  Thr  Asp  Asn  Met  Phe  Arg  Arg  Tyr  Ser  Phe
          115                      120                      125
Asp  Ile  Thr  His  Thr  Val  Lys  Ala  Val  Asn  Ile  Ile  Glu  Val  Arg  Phe
     130                      135                      140
Gln  Ser  Pro  Val  Val  Tyr  Ala  Asn  Gln  Arg  Ser  Glu  Arg  His  Thr  Ala
145                           150                      155                      160
Tyr  Trp  Val  Pro  Pro  Asn  Cys  Pro  Pro  Val  Gln  Asp  Gly  Glu  Cys
                    165                      170                           175
His  Val  Asn  Phe  Ile  Arg  Lys  Met  Gln  Cys  Ser  Phe  Gly  Trp  Asp  Trp
               180                      185                      190
Gly  Pro  Ser  Phe  Pro  Thr  Gln  Gly  Ile  Trp  Lys  Asp  Val  Arg  Ile  Glu
               195                      200                      205
Ala  Tyr  Asn  Val  Cys  His  Leu  Asn  Tyr  Phe  Met  Phe  Thr  Pro  Ile  Tyr
     210                      215                      220
Asp  Asn  Tyr  Met  Lys  Thr  Trp  Asn  Leu  Lys  Ile  Glu  Ser  Ser  Phe  Asp
225                           230                      235                      240
Val  Val  Ser  Ser  Lys  Leu  Val  Ser  Gly  Glu  Ala  Ile  Val  Ala  Ile  Pro
                    245                      250                      255
Glu  Leu  Asn  Ile  Gln  Gln  Thr  Asn  Asn  Ile  Glu  Leu  Gln  His  Gly  Glu
               260                      265                      270
Arg  Thr  Val  Glu  Leu  Phe  Val  Lys  Ile  Asp  Lys  Ala  Ile  Ile  Val  Glu
          275                      280                      285
Thr  Trp  Trp  Pro  His  Gly  His  Gly  Asn  Gln  Thr  Gly  Tyr  Asn  Met  Ser
     290                      295                      300
Val  Ile  Phe  Glu  Leu  Asp  Gly  Gly  Leu  Arg  Phe  Glu  Lys  Ser  Ala  Lys
305                           310                      315                      320
Val  Tyr  Phe  Arg  Thr  Val  Glu  Leu  Val  Glu  Glu  Pro  Ile  Gln  Asn  Ser
               325                      330                      335
Pro  Gly  Leu  Ser  Phe  Tyr  Phe  Lys  Ile  Asn  Gly  Leu  Pro  Ile  Phe  Leu
               340                      345                      350
Lys  Gly  Ser  Asn  Trp  Ile  Pro  Ala  Asp  Ser  Phe  Gln  Asp  Arg  Val  Thr
          355                      360                      365
Ser  Ala  Met  Leu  Arg  Leu  Leu  Leu  Gln  Ser  Val  Val  Asp  Ala  Asn  Met
     370                      375                      380
Asn  Ala  Leu  Arg  Val  Trp  Gly  Gly  Gly  Val  Tyr  Glu  Gln  Asp  Glu  Phe
385                           390                      395                      400
Tyr  Glu  Leu  Cys  Asp  Glu  Leu  Gly  Ile  Met  Ile  Trp  Gln  Asp  Phe  Met
               405                      410                      415
Phe  Ala  Cys  Ala  Leu  Tyr  Pro  Thr  Asp  Lys  Asp  Phe  Met  Asp  Ser  Val
               420                      425                      430
Arg  Glu  Glu  Val  Thr  His  Gln  Val  Arg  Arg  Leu  Lys  Ser  His  Pro  Ser
          435                      440                      445
Ile  Ile  Thr  Trp  Ser  Gly  Asn  Asn  Glu  Asn  Glu  Ala  Ala  Leu  Met  Met
     450                      455                      460
Gly  Trp  Tyr  Asp  Thr  Lys  Pro  Gly  Tyr  Leu  Gln  Thr  Tyr  Ile  Lys  Asp
465                           470                      475                      480
Tyr  Val  Thr  Leu  Tyr  Val  Lys  Asn  Ile  Arg  Thr  Ile  Val  Leu  Glu  Gly
               485                      490                      495
Asp  Gln  Thr  Arg  Pro  Phe  Ile  Thr  Ser  Ser  Pro  Thr  Asn  Gly  Ala  Lys
               500                      505                      510
Thr  Ile  Ala  Glu  Gly  Trp  Leu  Ser  Pro  Asn  Pro  Tyr  Asp  Leu  Asn  Tyr
          515                      520                      525
```

```
Gly  Asp  Val  His  Phe  Tyr  Asp  Tyr  Val  Ser  Asp  Cys  Trp  Asn  Trp  Arg
     530                 535                      540

Thr  Phe  Pro  Lys  Ala  Arg  Phe  Val  Ser  Glu  Tyr  Gly  Tyr  Gln  Ser  Trp
545                      550                 555                           560

Pro  Ser  Phe  Ser  Thr  Leu  Glu  Lys  Val  Ser  Ser  Glu  Glu  Asp  Trp  Ser
               565                      570                      575

Tyr  Arg  Ser  Ser  Phe  Ala  Leu  His  Arg  Gln  His  Leu  Ile  Asn  Gly  Asn
          580                      585                           590

Asn  Glu  Met  Leu  His  Gln  Ile  Glu  Leu  His  Phe  Lys  Leu  Pro  Asn  Ser
          595                 600                      605

Thr  Asp  Gln  Leu  Arg  Arg  Phe  Lys  Asp  Thr  Leu  Tyr  Leu  Thr  Gln  Val
     610                 615                      620

Met  Gln  Ala  Gln  Cys  Val  Lys  Thr  Glu  Thr  Glu  Phe  Tyr  Arg  Arg  Ser
625                      630                 635                           640

Arg  Ser  Glu  Ile  Val  Asn  Gly  Lys  Gly  His  Thr  Met  Gly  Ala  Leu  Tyr
               645                      650                           655

Trp  Gln  Leu  Asn  Asp  Ile  Trp  Gln  Ala  Pro  Ser  Trp  Ser  Ser  Leu  Glu
               660                      665                      670

Tyr  Gly  Gly  Lys  Trp  Lys  Met  Leu  His  Tyr  Phe  Ala  Arg  His  Phe  Phe
          675                      680                      685

Ala  Pro  Leu  Leu  Pro  Val  Gly  Phe  Glu  Asp  Lys  Asp  Met  Leu  Phe  Ile
690                           695                      700

Tyr  Gly  Ala  Ser  His  Leu  His  Ser  Asp  Gln  Gln  Met  Met  Leu  Thr  Val
705                      710                      715                      720

Arg  Val  His  Thr  Trp  Ser  Ser  Leu  Glu  Leu  Val  Cys  Ser  Glu  Ser  Thr
                    725                      730                      735

Asn  Pro  Phe  Val  Ile  Lys  Ala  Gly  Glu  Ser  Val  Leu  Leu  Tyr  Thr  Lys
               740                      745                      750

Pro  Val  Pro  Glu  Leu  Leu  Lys  Gly  Cys  Pro  Gly  Cys  Thr  Arg  Gln  Ser
          755                      760                      765

Cys  Val  Val  Ser  Phe  Tyr  Leu  Ser  Thr  Asp  Gly  Glu  Leu  Leu  Ser  Pro
     770                      775                      780

Ile  Asn  Tyr  His  Phe  Leu  Ser  Ser  Leu  Lys  Asn  Ala  Lys  Gly  Leu  His
785                      790                      795                      800

Lys  Ala  Asn  Ile  Thr  Ala  Thr  Ile  Ser  Gln  Gln  Gly  Asp  Thr  Phe  Val
               805                      810                      815

Phe  Asp  Leu  Lys  Thr  Ser  Ala  Val  Ala  Pro  Phe  Val  Trp  Leu  Asp  Val
          820                      825                      830

Gly  Ser  Ile  Pro  Gly  Arg  Phe  Ser  Asp  Asn  Gly  Phe  Leu  Met  Thr  Glu
          835                      840                      845

Lys  Thr  Arg  Thr  Val  Phe  Phe  Tyr  Pro  Trp  Lys  Pro  Thr  Ser  Lys  Ser
     850                      855                      860

Glu  Leu  Glu  Gln  Ser  Phe  His  Val  Thr  Ser  Leu  Ala  Asp  Thr  Tyr
865                      870                      875
```

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: primer ( x i ) SEQUENCE DESCRIPTION: SEQ ID NO:3:

ACTGTATTCT TTTACCCCTG                                                                                                    20

( 2 ) INFORMATION FOR SEQ ID NO:4:

( i ) SEQUENCE CHARACTERISTICS:
     ( A ) LENGTH: 20 base pairs
     ( B ) TYPE: nucleic acid
     ( C ) STRANDEDNESS: single
     ( D ) TOPOLOGY: linear ( i i ) MOLECULE TYPE: primer ( x i ) SEQUENCE DESCRIPTION: SEQ ID NO:4:

AAGTGGCTAA CGAGACACCT                                                                                                    20

( 2 ) INFORMATION FOR SEQ ID NO:5:

( i ) SEQUENCE CHARACTERISTICS:
     ( A ) LENGTH: 17 base pairs
     ( B ) TYPE: nucleic acid
     ( C ) STRANDEDNESS: single
     ( D ) TOPOLOGY: linear ( i i ) MOLECULE TYPE: primer ( x i ) SEQUENCE DESCRIPTION: SEQ ID NO:5:

GGNTTYGARG AYAARGA                                                                                                       17

( 2 ) INFORMATION FOR SEQ ID NO:6:

( i ) SEQUENCE CHARACTERISTICS:
     ( A ) LENGTH: 17 base pairs
     ( B ) TYPE: nucleic acid
     ( C ) STRANDEDNESS: single
     ( D ) TOPOLOGY: linear ( i i ) MOLECULE TYPE: primer ( x i ) SEQUENCE DESCRIPTION: SEQ ID NO:6:

TARTTRTCRT ADATNGG                                                                                                       17

( 2 ) INFORMATION FOR SEQ ID NO:7:

( i ) SEQUENCE CHARACTERISTICS:
     ( A ) LENGTH: 17 base pairs
     ( B ) TYPE: nucleic acid
     ( C ) STRANDEDNESS: single
     ( D ) TOPOLOGY: linear ( i i ) MOLECULE TYPE: primer ( x i ) SEQUENCE DESCRIPTION: SEQ ID NO:7:

CCRAARTCYT TRTCNGT                                                                                                       17

( 2 ) INFORMATION FOR SEQ ID NO:8:

( i ) SEQUENCE CHARACTERISTICS:
     ( A ) LENGTH: 17 base pairs
     ( B ) TYPE: nucleic acid
     ( C ) STRANDEDNESS: single
     ( D ) TOPOLOGY: linear ( i i ) MOLECULE TYPE: primer ( x i ) SEQUENCE DESCRIPTION: SEQ ID NO:8:

ATHAARGAYC CNTAYTA                                                                                                       17

( 2 ) INFORMATION FOR SEQ ID NO:9:

( i ) SEQUENCE CHARACTERISTICS:
 ( A ) LENGTH: 44 base pairs
 ( B ) TYPE: nucleic acid
 ( C ) STRANDEDNESS: single
 ( D ) TOPOLOGY: linear ( i i ) MOLECULE TYPE: primer ( x i ) SEQUENCE DESCRIPTION: SEQ ID NO:9:

TCCTTCTTTG CCCCCCTGCT GCCTGTGGGC TTTGAGGACA AGGA   44

( 2 ) INFORMATION FOR SEQ ID NO:10:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( i i ) MOLECULE TYPE: primer ( x i ) SEQUENCE DESCRIPTION: SEQ ID NO:10:

CTGTTCATCT ATGGCGCCTC TGACCTGCAC TCTGAC   36

( 2 ) INFORMATION FOR SEQ ID NO:11:

( i ) SEQUENCE CHARACTERISTICS:
  ( A ) LENGTH: 44 base pairs
  ( B ) TYPE: nucleic acid
  ( C ) STRANDEDNESS: single
  ( D ) TOPOLOGY: linear ( i i ) MOLECULE TYPE: primer ( x i ) SEQUENCE DESCRIPTION: SEQ ID NO:11:

GACTGGAGCA GTCCTTCCAT GTGACCTCCC TGGCTGACAC CTAC   44

( 2 ) INFORMATION FOR SEQ ID NO:12:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: primer ( x i ) SEQUENCE DESCRIPTION: SEQ ID NO:12:

CACAAAGAGC TCAACAGTCC TTTC   24

( 2 ) INFORMATION FOR SEQ ID NO:13:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: primer ( x i ) SEQUENCE DESCRIPTION: SEQ ID NO:13:

AGGTCAATGT TGTTTGTCTG CTGT   24

( 2 ) INFORMATION FOR SEQ ID NO:14:

( i ) SEQUENCE CHARACTERISTICS:
  ( A ) LENGTH: 32 base pairs
  ( B ) TYPE: nucleic acid
  ( C ) STRANDEDNESS: single
  ( D ) TOPOLOGY: linear ( i i ) MOLECULE TYPE: primer ( x i ) SEQUENCE DESCRIPTION: SEQ ID NO:14:

GCTCTAGAAA CATGAAGTAG TTCAGATGAC AA  32

( 2 ) INFORMATION FOR SEQ ID NO:15:

( i ) SEQUENCE CHARACTERISTICS:
          ( A ) LENGTH: 25 base pairs
          ( B ) TYPE: nucleic acid
          ( C ) STRANDEDNESS: single
          ( D ) TOPOLOGY: linear ( i i ) MOLECULE TYPE: primer ( x i ) SEQUENCE DESCRIPTION: SEQ ID NO:15:

CTGGATCCAT GCTNCATYAT YTTSC  25

( 2 ) INFORMATION FOR SEQ ID NO:16:

( i ) SEQUENCE CHARACTERISTICS:
          ( A ) LENGTH: 28 base pairs
          ( B ) TYPE: nucleic acid
          ( C ) STRANDEDNESS: single
          ( D ) TOPOLOGY: linear ( i i ) MOLECULE TYPE: primer ( x i ) SEQUENCE DESCRIPTION: SEQ ID NO:16:

ACGTCGSCGG YTTCCANGGR TARAARAA  28

( 2 ) INFORMATION FOR SEQ ID NO:17:

( i ) SEQUENCE CHARACTERISTICS:
          ( A ) LENGTH: 9 amino acids
          ( B ) TYPE: amino acid
          ( C ) TOPOLOGY: linear ( i i ) MOLECULE TYPE: peptide ( x i ) SEQUENCE DESCRIPTION: SEQ ID NO:17:

Phe Thr Pro Ile Tyr Asp Asn Tyr Met
                     5

( 2 ) INFORMATION FOR SEQ ID NO:18:

( i ) SEQUENCE CHARACTERISTICS:
          ( A ) LENGTH: 6 amino acids
          ( B ) TYPE: amino acid
          ( C ) TOPOLOGY: linear ( i i ) MOLECULE TYPE: peptide ( x i ) SEQUENCE DESCRIPTION: SEQ ID NO:18:

Phe Thr Pro Ile Tyr Asp
              5

( 2 ) INFORMATION FOR SEQ ID NO:19:

( i ) SEQUENCE CHARACTERISTICS:
          ( A ) LENGTH: 15 amino acids
          ( B ) TYPE: amino acid
          ( C ) TOPOLOGY: linear ( i i ) MOLECULE TYPE: peptide ( x i ) SEQUENCE DESCRIPTION: SEQ ID NO:19:

Leu Phe Ile Tyr Gly Ala Ser Asp Leu His Ser Asp Gln Gln Met
                 5                   10                  15

( 2 ) INFORMATION FOR SEQ ID NO:20:

( i ) SEQUENCE CHARACTERISTICS:
                ( A ) LENGTH: 9 amino acids
                ( B ) TYPE: amino acid
                ( C ) TOPOLOGY: linear ( i i ) MOLECULE TYPE: peptide ( x i ) SEQUENCE DESCRIPTION: SEQ ID NO: 20:

Gly Ala Ser Asp Leu His Ser Phe Gln
                 5

( 2 ) INFORMATION FOR SEQ ID NO:21:

( i ) SEQUENCE CHARACTERISTICS:
                ( A ) LENGTH: 16 amino acids
                ( B ) TYPE: amino acid
                ( C ) TOPOLOGY: linear ( i i ) MOLECULE TYPE: peptide ( x i ) SEQUENCE DESCRIPTION: SEQ ID NO:21:

Ser Phe Phe Ala Pro Leu Leu Pro Val Gly Phe Glu Asp Lys Asp
                 5                   10                  15
Thr ( 2 ) INFORMATION FOR SEQ ID NO:22:

( i ) SEQUENCE CHARACTERISTICS:
                ( A ) LENGTH: 6 amino acids
                ( B ) TYPE: amino acid
                ( C ) TOPOLOGY: linear ( i i ) MOLECULE TYPE: peptide ( x i ) SEQUENCE DESCRIPTION: SEQ ID NO:22:

Leu His Tyr Phe Ala Arg
                 5

( 2 ) INFORMATION FOR SEQ ID NO:23:

( i ) SEQUENCE CHARACTERISTICS:
                ( A ) LENGTH: 9 amino acids
                ( B ) TYPE: amino acid
                ( C ) TOPOLOGY: linear ( i i ) MOLECULE TYPE: peptide ( x i ) SEQUENCE DESCRIPTION: SEQ ID NO:23:

Ile Ile Lys Asp Pro Tyr Tyr Arg Arg
                 5

( 2 ) INFORMATION FOR SEQ ID NO:24:

( i ) SEQUENCE CHARACTERISTICS:
                ( A ) LENGTH: 10 amino acids
                ( B ) TYPE: amino acid
                ( C ) TOPOLOGY: linear ( i i ) MOLECULE TYPE: peptide ( x i ) SEQUENCE DESCRIPTION: SEQ ID NO:24:

Thr Val Phe Phe Tyr Pro Trp Lys Pro Met
                 5                   10

( 2 ) INFORMATION FOR SEQ ID NO:25:

( i ) SEQUENCE CHARACTERISTICS:
        ( A ) LENGTH: 11 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:25:

Phe Lys Asp Thr Leu Tyr Leu Thr Gln Val Met
             5                  10

( 2 ) INFORMATION FOR SEQ ID NO:26:

( i ) SEQUENCE CHARACTERISTICS:
        ( A ) LENGTH: 16 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:26:

Thr Glu Leu Glu Gln Ser Phe His Val Thr Ser Leu Ala Asp Thr
             5                      10                  15

Tyr ( 2 ) INFORMATION FOR SEQ ID NO:27:

( i ) SEQUENCE CHARACTERISTICS:
        ( A ) LENGTH: 13 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:27:

Phe Ala Cys Ala Leu Tyr Pro Thr Asp Lys Asp Phe Met
             5                      10

( 2 ) INFORMATION FOR SEQ ID NO:28:

( i ) SEQUENCE CHARACTERISTICS:
        ( A ) LENGTH: 13 amino acids
        ( B ) TYPE: amino acid
        ( C ) TOPOLOGY: linear ( i i ) MOLECULE TYPE: peptide ( x i ) SEQUENCE DESCRIPTION: SEQ ID NO:28:

Phe Ala Cys Ala Leu Tyr Pro Thr Asp Lys Asp Phe Gly
             5                      10